(12) United States Patent
Hershberger

(10) Patent No.: US 7,220,264 B1
(45) Date of Patent: May 22, 2007

(54) MINIMALLY INVASIVE REAMER

(75) Inventor: Troy Hershberger, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 360 days.

(21) Appl. No.: 10/387,108

(22) Filed: Mar. 12, 2003

(51) Int. Cl.
*A61B 17/00* (2006.01)

(52) U.S. Cl. ..................................... 606/81

(58) Field of Classification Search ............ 606/79–81
See application file for complete search history.

(56) References Cited

U.S. PATENT DOCUMENTS

| 1,923,177 A | 8/1933 | Tucker |
| 3,412,733 A | 11/1968 | Ross |
| 3,630,204 A | 12/1971 | Fishbein |
| 3,633,583 A | 1/1972 | Fishbein |
| 3,702,611 A | 11/1972 | Fishbein |
| 4,011,025 A | 3/1977 | Kress |
| 4,023,572 A | 5/1977 | Weigand et al. |
| 4,116,200 A | 9/1978 | Braun et al. |
| 4,131,116 A | 12/1978 | Hedrick |
| 4,199,284 A | 4/1980 | Kress et al. |
| 4,239,427 A | 12/1980 | Walton, II |
| 4,621,637 A | 11/1986 | Fishbein |
| 4,811,632 A | 3/1989 | Salyer |
| 5,030,219 A | 7/1991 | Matsen, III et al. |
| 5,032,132 A | 7/1991 | Matsen, III et al. |
| 5,092,719 A | 3/1992 | Zsiger |
| 5,100,267 A | 3/1992 | Salyer |
| 5,116,165 A | 5/1992 | Salyer |
| 5,171,312 A | 12/1992 | Salyer |
| 5,171,313 A | 12/1992 | Salyer |
| 5,203,653 A | 4/1993 | Kudla |
| 5,236,289 A | 8/1993 | Salyer |
| 5,236,433 A | 8/1993 | Salyer |
| 5,282,804 A | 2/1994 | Salyer |
| 5,295,992 A | 3/1994 | Cameron |
| 5,299,893 A | 4/1994 | Salyer et al. |
| 5,376,092 A | 12/1994 | Hein et al. |
| 5,462,548 A | 10/1995 | Pappas et al. |
| 5,501,686 A | 3/1996 | Salyer |
| 5,562,702 A | 10/1996 | Huitema et al. |

(Continued)

FOREIGN PATENT DOCUMENTS

EP 0139356 * 2/1985

OTHER PUBLICATIONS

Delta Reverse Shoulder System (Surgical Technique), DePuy Orthopaedics, Inc., 2001, 29 pages.

(Continued)

*Primary Examiner*—Eduardo C. Robert
*Assistant Examiner*—Michael J. Araj
(74) *Attorney, Agent, or Firm*—Harness, Dickey & Pierce, P.L.C.

(57) ABSTRACT

A reamer for reaming of a acetabulum during a minimally invasive procedure. Generally, the reamer, particularly the reamer head, can be inserted and removed through a substantially small incision without trauma to the tissue surrounding the incision. The reamer, generally includes a reaming or scraping portion, which are aligned substantially along a single meridian of a hemisphere. The reamer further includes stabilizing portions to assist in ensuring a selected reaming orientation. Also, protective wings assist in removing the reamer.

34 Claims, 11 Drawing Sheets

U.S. PATENT DOCUMENTS

| | | | |
|---|---|---|---|
| 5,624,447 A | 4/1997 | Myers | |
| 5,658,290 A * | 8/1997 | Lechot | 606/80 |
| 5,709,688 A | 1/1998 | Salyer | |
| 5,755,719 A | 5/1998 | Frieze et al. | |
| 5,817,096 A | 10/1998 | Salyer | |
| 5,824,181 A | 10/1998 | Salyer et al. | |
| 5,897,558 A * | 4/1999 | Frieze et al. | 606/81 |
| 5,947,805 A | 9/1999 | Van Osenbruggen | |
| 5,976,148 A | 11/1999 | Charpenet et al. | |
| 5,980,170 A * | 11/1999 | Salyer | 408/239 R |
| 6,001,105 A | 12/1999 | Salyer | |
| 6,045,302 A | 4/2000 | Orr | |
| 6,102,915 A | 8/2000 | Bresler et al. | |
| 6,132,469 A | 10/2000 | Schroeder | |
| 6,168,600 B1 | 1/2001 | Grace et al. | |
| 6,221,076 B1 | 4/2001 | Albrektsson et al. | |
| 6,245,074 B1 | 6/2001 | Allard et al. | |
| 6,250,858 B1 | 6/2001 | Salyer | |
| 6,283,972 B1 | 9/2001 | Riley | |
| 6,312,325 B1 | 11/2001 | Van Osenbruggen | |
| 6,409,732 B1 | 6/2002 | Salyer | |
| 6,416,553 B1 | 7/2002 | White et al. | |
| 6,428,543 B1 | 8/2002 | Salyer | |
| 6,458,161 B1 | 10/2002 | Gibbs et al. | |
| 2002/0099380 A1 | 7/2002 | Salyer et al. | |
| 2003/0135219 A1* | 7/2003 | Salyer et al. | 606/81 |
| 2003/0163135 A1 | 8/2003 | Hathway | |
| 2003/0212402 A1 | 11/2003 | White et al. | |
| 2003/0220647 A1 | 11/2003 | McCallum et al. | |
| 2004/0097947 A1 | 5/2004 | Wolford et al. | |
| 2005/0216020 A1 | 9/2005 | Orton | |
| 2006/0129157 A1 | 6/2006 | Desarzens et al. | |

OTHER PUBLICATIONS

Delta Medial Offset Total Shoulder (Product Rationale-Surgical Technique), DePuy Orthopaedics, Inc., 2001, 19 pages.

http://www.extremities.org/patient_info/rsp.html, Reverse Shoulder Prosthesis, printed Oct. 27, 2004, 5 pages.

Global Advantage Shoulder Arthroplasty System (Design Rationale); DePuy Orthopaedics, Inc., no date, 6 pages.

Global Total Shoulder Arthroplasty System, DePuy Orthopaedics, Inc., 1994, 3 pages.

Global Advantage Shoulder Arthroplasty System (Surgical Technique), DePuy Orthopaedics, 2000, 32 pages.

* cited by examiner

MINIMALLY INVASIVE REAMER

FIELD

The following relates to a reamer for an orthopedic procedure, more particularly, to a reamer for a minimally invasive reaming of an anatomical structure during an orthopedic procedure.

BACKGROUND

Many portions of the anatomy, particularly the human anatomy, articulate relative one another. Generally, articulation occurs between two proximal or adjacent anatomical portions, such as bones. For example, a hip joint is formed by the articulation of the head of the femur with the acetabulum defined by the pelvis.

In a natural or uninjured hip joint, the femoral head articulates substantially smoothly with the acetabulum. Both the femoral head and the acetabulum are generally covered with cartilage, such that the articulation of the hip joint is substantially smooth and pain free. Nevertheless, due to injury, aging, wear, or other degenerative issues, the joint may become worn, such that articulation of the hip joint is painful or impractical. When such injuries or deteriorations occur, it is sometimes possible to replace the natural hip joint with an artificial hip joint. The replacement or artificial hip joint may include a prosthetic femoral head and a prosthetic acetabulum, including an acetabular cup. Although both may be replaced, it will be understood that either one or the other may be replaced and the natural portion of the other left in place.

If it is selected to replace the acetabulum of an individual, the acetabulum is often reamed. Specifically, the acetabulum is reamed, such that the natural tissue, including the cartilage is removed. This prepares the acetabulum for an acetabular implant. The acetabular cup may include an outer shell and an inner lining or only one or the other. Nevertheless, it is often desired to remove the injured or deteriorated natural anatomical structures to prepare the acetabulum for reception of the acetabular implant.

Generally, removing or reaming of the acetabulum requires a substantially invasive incision to allow for a clear and open path to the acetabulum by the tools required to ream the acetabulum. Generally, a large incision allows for complete dislocation of the femoral head from the acetabulum to allow for reaming of the acetabulum.

Therefore, it is desirable to provide a method and tool for a minimally invasive procedure for reaming the acetabulum to prepare it for reception of an acetabular prosthetic.

SUMMARY

A reamer that allows for reaming of the acetabulum during a minimally invasive procedure. Generally, the reamer, particularly the reamer head, may be inserted and removed through a substantially small incision substantially without trauma to the tissue surrounding the incision. The reamer, generally includes a reaming or scraping portion, which are aligned substantially along a single meridian of a hemisphere. This provides a portion of the reamer that is left smooth to minimize injury to soft tissue surrounding the incision.

The reamer may be provided substantially hemispherical to provide for ease of reaming of the acetabulum and for a substantially stable reaming of the acetabulum. Regardless that the cutting portion defines only a portion of the hemisphere. In addition, the reamer may include openings that allow for viewing of the acetabulum as it is being reamed. Specifically, openings or transparent areas are provided in the reamer, such that the acetabulum can be viewed through the reamer, rather than requiring the removal of the reamer from the acetabulum to review the progress of the reaming procedure.

According to various embodiments, a reamer for use in a minimally invasive procedure to ream a selected anatomical portion is provided. The reamer includes a cutting section defining a portion of a sphere on a first side of a plane. The reamer further includes a protection member that extends on a second side of said plane to minimize trauma during ingress and egress of the reamer. The protection member is adapted to maintain tissue, that surrounds the selected anatomical portion, at a selected distance during ingress and egress of the reamer.

According to a various embodiment, an acetabular reamer for entering through a soft tissue and reaming an acetabular of an individual is disclosed. The acetabular reamer includes a cutting section which defines a first portion of a sphere extending from a first plane. The acetabular reamer further includes a stabilizing member extending from the cutting section and defining a second portion of the sphere. A wing extends from the stabilizing member. The wing protects the soft tissue during insertion and removal of the acetabular reamer from the acetabulum.

According to various other embodiments, a method for reaming acetabulum that is generally covered by a soft tissue, with a reamer. The method includes providing a portal, having a first dimension through the soft tissue. A portion of the soft tissue is moved adjacent the portal to allow the reamer through the portal. Generally, the soft tissue is moved with a first portion of the reamer while a second portion of the reamer passes through the soft tissue. The reamer is then passed through the portal. Generally, the reamer includes a second dimension that is greater than the first dimension of the portal. Moving the soft tissue with the first portion of the reamer generally provides a substantially minimally invasive passing of the reamer to the portal.

According to various embodiments a reamer for reaming an anatomical portion includes a member defining a portion of a sphere extending from a plane in a first direction. The reamer further includes a substantially continuous rim extending from the member defining a perimeter. A viewing area is defined by the member and the rim. The anatomical portion is viewable through the viewing area.

Further areas of applicability of the present disclosure will become apparent from the detailed description provided hereinafter. It should be understood that the detailed description and various examples, while indicating various embodiments of the invention, are intended for purposes of illustration only and are not intended to limit the scope of the following claims.

BRIEF DESCRIPTION OF THE FIGURES

The present invention will become more fully understood from the detailed description and the accompanying drawings, wherein.

DETAILED DESCRIPTION OF VARIOUS EMBODIMENTS

Figure 1:
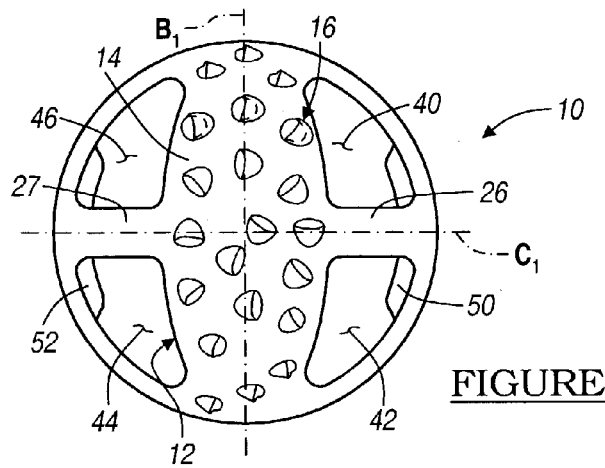
FIG. 1 is a bottom or distal plan view of a reamer according to an embodiment.
Figure 2:
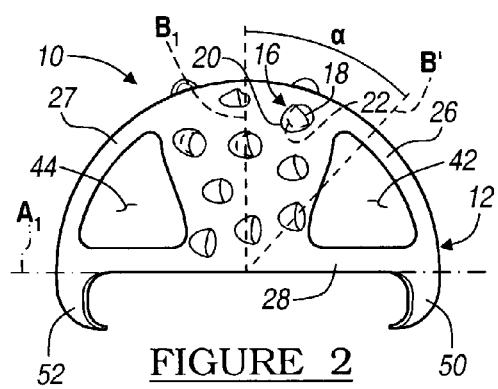
FIG. 2 is a side plan view of the reamer of FIG. 1, along the meridian of the scraper teeth.
Figure 3:
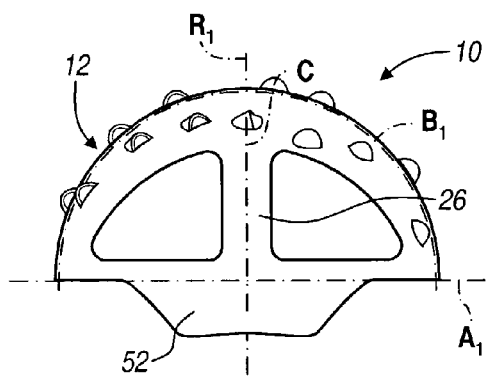
FIG. 3 is a side plan view of the reamer of FIG. 1, along a meridian, which intersects the meridian of the scraper teeth.
Figure 4:
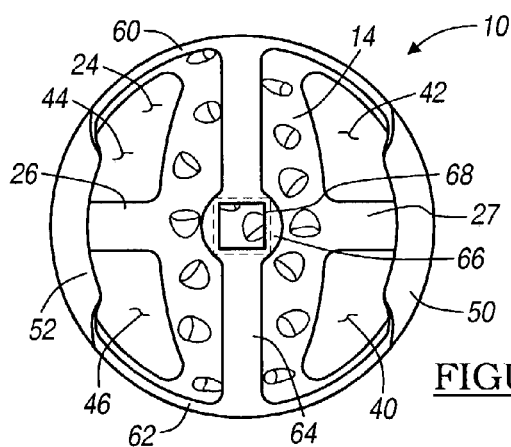
FIG. 4 is a top plan view of the reamer of FIG. 1.
Figure 5:
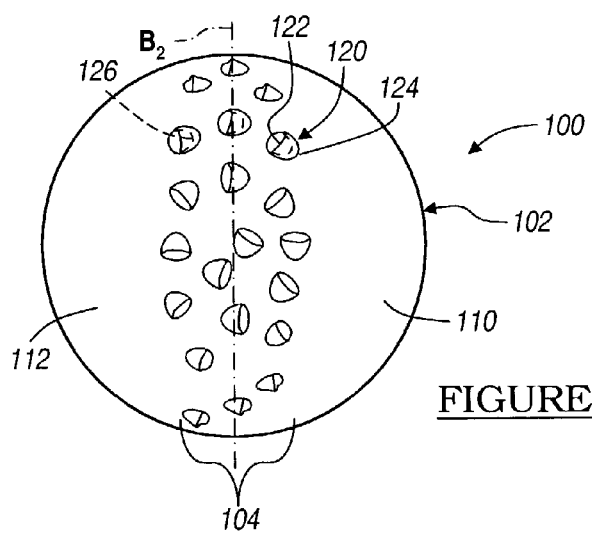
FIG. 5 is a bottom plan view of a reamer according to an alternative embodiment.
Figure 6:
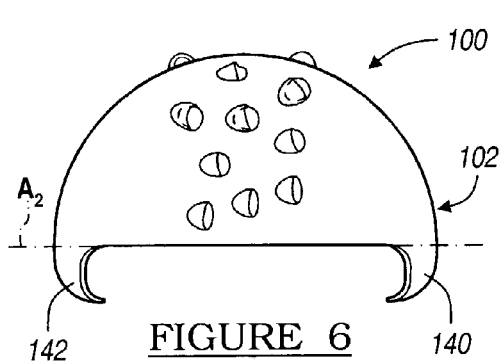
FIG. 6 is a side plan view of the reamer of FIG. 5, along the meridian of the scraper teeth.
Figure 7:
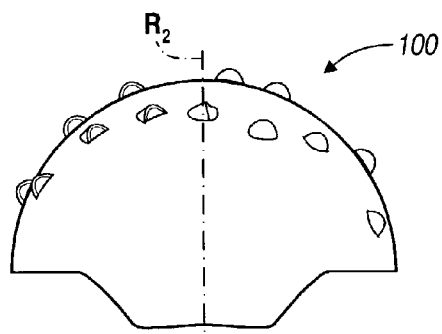
FIG. 7 is a side plan view of the reamer of FIG. 5, along a meridian, which intersects the meridian of the scraper teeth.
Figure 8:
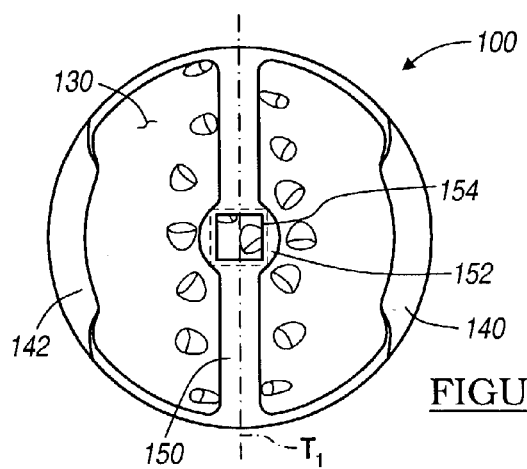
FIG. 8 is a top plan view of the reamer according to the embodiment illustrated in FIG. 5.
Figure 9:
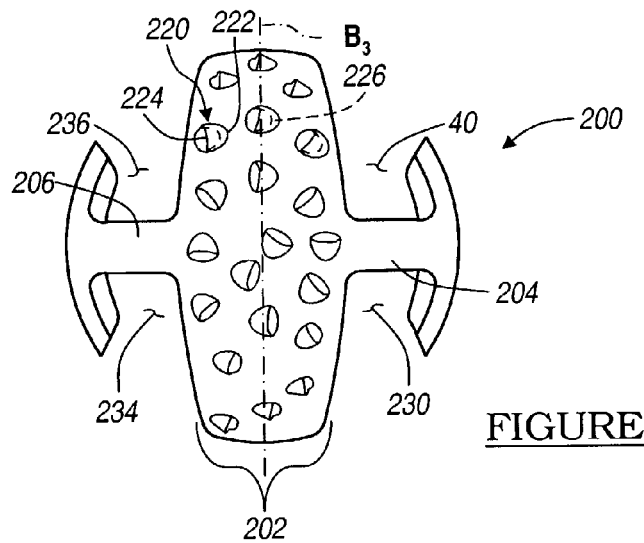
FIG. 9 is a bottom plan view of a reamer according to an additional alternative embodiment.
Figure 10:
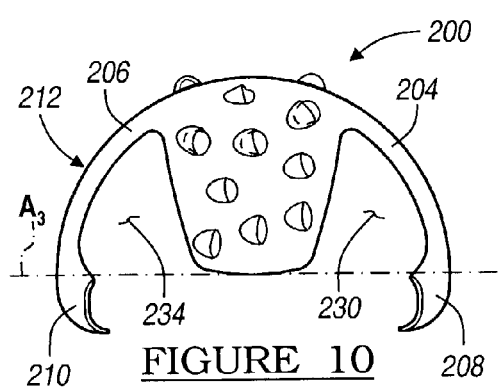
FIG. 10 is a side plan view of the reamer of FIG. 9, along the meridian of the scraper teeth.
Figure 11:
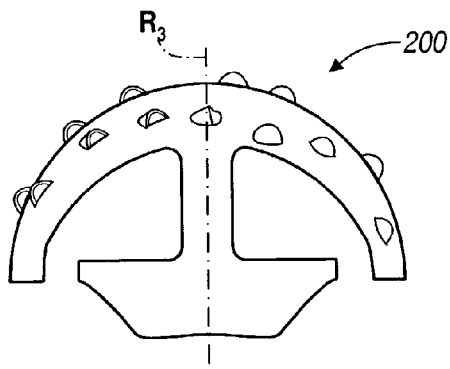
FIG. 11 is a side plan view of the reamer of FIG. 9, along a meridian, which intersects the meridian of the scraper teeth.
Figure 12:
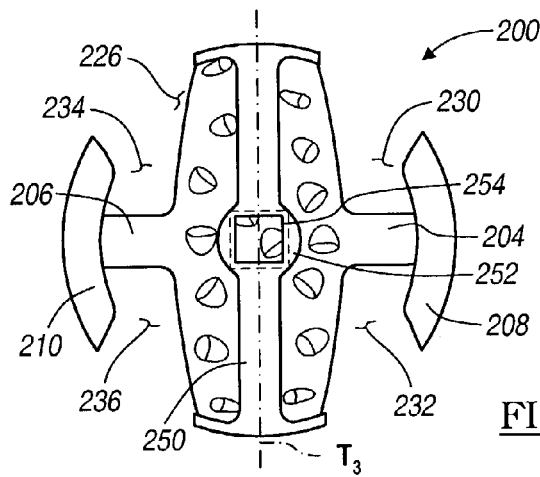
FIG. 12 is a top plan view of the reamer illustrated in FIG. 9.

The following description of various embodiment(s) is merely exemplary in nature and is in no way intended to limit the application or uses. Although the following description defines exemplary reamers particularly for reaming an acetabulum of the anatomy, it will be understood that the following description may be used for various other applications. For example, a humeral reamer or a reamer for reaming an intramedullary canal of a bone may also be provided with the following described elements.

With reference to FIGS. 1–4, a reamer 10 for reaming an anatomical portion is illustrated. Generally, the reamer 10 defines a substantial portion of a sphere 12 above a plane $A_1$. The portion of the sphere 12 may be any portion and may include a hemisphere. The reamer 10 further defines a first meridian $B_1$, which is defined by a cutting or reaming portion 14. The reamer 10 further defines a second meridian $C_1$, which substantially defines a stabilizing or guarding meridian.

Formed substantially along the first meridian $B_1$ is the cutting surface 14. The cutting surface 14 defines a first portion of the hemisphere 12. Generally, the cutting surface 14 extends about 1° to about 160° of the hemisphere 12 of the reamer 10. That is, the cutting surface generally extends an angle α, generally about 1° to about 80°, to a side or between meridian $B_1$ and meridian B'. Nevertheless, the cutting surface generally extends at least 90° to about 200° along the meridian $B_1$.

The cutting surface 14 defines a plurality of cutting portions 16. The cutting portions 16 may be provided in any appropriate number appropriate for reaming an anatomical portion, such as an acetabulum. It will be understood that various different sizes of the reamer 10 may be provided and differing numbers of the cutting portions 16 may be provided on the differing sizes of the reamer 10. Moreover, differing numbers of the cutting portion 16 can be provided depending upon the size or the desired coverage of the cutting portions 16.

Generally, the cutting portions 16 include a cutting surface or edge 18 followed by a ramp or following surface 20. The cutting edge 18 is adjacent to an opening 22. The cutting edge 18 generally faces or defines a leading edge over the reamer 10. That is, in operation the reamer 10 is rotated about an axis of rotation $R_1$ in a specified direction, such that the cutting edge 18 first engages and then cuts a selected surface or material. Therefore, the cutting edge 18 generally faces the direction of rotation of the reamer 10.

As the cutting edge 18 cuts the material the opening 22 allows the cut material to pass through or into the reamer 10. Specifically, the reamer 10, defining the hemisphere 12, is substantially open or empty, such that material may be moved into an interior 24 of the hemisphere 12 and substantially away from the anatomical structure being cut. Therefore, as the acetabulum is cut, the cut or debris material is removed from the surface of the acetabulum, thereby providing a clean surface for further reaming. Specifically, as a first portion of the acetabulum is cut with the cutting edge 18, the material is pushed or drawn into the interior 24 of the reamer 10, such that the surface of the acetabulum is left substantially clean for additional reaming until the procedure is completed.

Extending substantially perpendicular to the cutting or reaming surface 14 and along the second meridian $C_1$ is a first stabilization bar or stabilizing portion 26 and a second stabilizing bar or portion 27. Although only two stabilization portions 26 and 27 are illustrated, any appropriate number may be provided. Generally, the stabilization portions 26 and 27 extend from the cutting surface 14 to further define the hemisphere 12. That is, the stabilization portions 26 and 27 extend along the meridian $C_1$ towards the plane $A_1$ along the hemisphere 12. At or near the plane $A_1$ extending between the stabilization portions 26 and 27 and the cutting surface 14 is a rim 28. The rim 28 substantially lies upon the plane $A_1$ and defines an equator of the hemisphere 12. Therefore, the stabilization portions 26 and 27 are substantially interconnected along the plane A with the cutting section 14 by the rim 28.

The stabilization portions 26 and 27, which may also cooperate with the rim 28, also define a protection portion. As described further herein, as the reamer 10 is inserted through an incision, the stabilization portions 26 and 27 cooperate with other portions of the reamer 10 to form a tissue track. The soft tissue surrounding the incision is pushed or moved away from the cutting area 14 as the reamer 10 is inserted through the incision.

The hemisphere 12 is at least partially defined by the cutting area 14 and the stabilization portions 26 and 27. Specifically, the stabilization portions 26 and 27 extend through a portion of the hemisphere 12 not specifically defined by a portion of the cutting area 14. As described further herein, the acetabulum is substantially hemispherically shaped. Moreover, it is desired to produce a substantially hemispherical shape of the acetabulum for preparation of receiving an acetabular implant. Therefore, the stabilization bars 26 and 27 may engage the acetabulum in areas where the cutting area 14 is not simultaneously engaged to hold the reamer 10 in a selected axial orientation. In this way, the stabilization bars 26 allow the reamer 10 to be provided in a substantially small area, yet be stabilized in a selected axial position. Moreover, the cutting area 14 defines only a small portion of the hemisphere 12 of the reamer 10. Therefore, the stabilization bars 26 are able to provide additional support to further define the hemisphere 12 of the reamer 10, thereby allowing the reamer 10 to be substantially stable during the reaming process. The specific orientation has generally relative the axis of rotation R. Therefore, the axis of rotation $R_1$ may be positioned at a selected position relative to the acetabulum and held substantially in that position for the reaming procedure. Therefore, the stabilization bars 26 and 27 cooperate with the cutting area 14 such that the axis of rotation $R_1$ can be held at a single position relative to the acetabulum.

Defined between the cutting surface 14 and the stabilization portions 26 and 27 are a plurality of windows or voids 40, 42, 44, and 46. The voids 40–46 define portions of the hemisphere 12, which are substantially not present. The voids 40–46, being defined by the cutting surface 14 and the stabilization bars 26 and 27, substantially complete the hemisphere 12. Although because the voids 40–46 are substantially not solid, light is able to transmit or reflect from material positioned on the side opposite the viewer relative to the reamer 10. This allows the reamer 10 to be positioned in a selected anatomical portion, such as an acetabulum, and allows the user to view the acetabulum on the opposite side of the reamer 10, while the reamer 10 is in place. Moreover, as the reamer 10 rotates, around the axis of rotation $R_1$, the voids 40–46 rotate thus substantially allowing viewing of the entire area on the opposite side of the reamer 10 from the user. Generally, the voids 40–46 allow for viewing of each quadrant of the area substantially parallel to the plane $A_1$ on the side of the reamer 10 opposite the user.

Extending up from the reamer 10, extending beyond the plane $A_1$ away from the hemisphere 12 of the reamer 10 are a first guarding portion or wing 50 and a second guarding portion or wing 52. The wings 50 and 52 extend beyond the plane $A_1$ and towards the axis of rotation $R_1$. The edges of the wings 50 and 52 are substantially rounded and smooth. Therefore, the wings 50 and 52 define an arc extending opposite the hemisphere 12, relative to the plane $A_1$. At least a portion of the reamer 10, which extends opposite the hemisphere 12, is defined and protected by the wings 50 and 52. As described further herein, the wings 50 and 52 provide for protection or minimization in injury to soft tissue of the area surrounding an incision to gain access to an acetabulum.

The wings 50 and 52 extend from the rim 28 substantially along the meridian $C_1$ defined by the first and second stabilization bars 26 and 27. Moreover, the first wing 50 extends substantially aligned with the first stabilization bar 26 while the second wing 52 extends substantially aligned with the second stabilization bar 27. The stabilization bars 26 and 27 cooperate with the respective wing 50 and 52 to provide the tissue track or protection area for ingress and egress of the reamer 10. As mentioned above and described further herein, the stabilization bars assist in holding the soft tissue away from the cutting area 14. In addition, the wings 50 and 52 assist in moving the soft tissue away from the cutting area 14 during egression of the reamer 10. Therefore, the stabilization bar 26 and 27 cooperate with the wings 50 and 52 to minimize trauma to the soft tissue, such as tearing, during ingression and egression of the reamer 10.

The cutting surface 14 substantially terminates in a first side 60 and a second side 62. Extending between the first side 60 and the second side 62 is a tool mounting bar or portion 64. The tool mounting bar 64 allows for attachment of a tool to operate the reamer 10 during a procedure. The tool mounting bar 64 may be provided in any appropriate manner to allow for mounting of a tool, described further herein, which can rotate the reamer 10 around the axis of rotation $R_1$. For example, the tool engagement bar 64 may define a tool engaging section 66. The tool engaging section 66 may further define a tool engaging bore 68. The tool engaging bore 68 may be any appropriate shape or size, such that a rotational force of the tool, is translated to the reamer 10, such that the rotational force of the tool is translated to the cutting surface 14, and the reamer 10 rotates around the axis of rotation R and the cutting edges 18 cut the acetabulum. For example, the tool engaging bore 68 may be substantially square, rectangular, hexagonal, or other polygonal shape, such that a tool portion having a complementary shape engages the tool engaging bore 68. In this way, the tool can transfer force to the reamer 10 and allow the reamer 10 to ream an acetabulum, thereby preparing it for an acetabular implant.

With reference to FIGS. 5–8, a reamer 100 according to an alternative embodiment is illustrated. The reamer 100 can be used for reaming an acetabulum of a pelvis. The reamer 100, generally defines a hemisphere 102 that extends above a plane $A_2$. The reamer 100 further includes a cutting or reaming area 104, which extends substantially along and adjacent to a first meridian $B_2$. Although the cutting area 104 may be any appropriate width, the cutting area 104 extends about 1° to about 80°, either side of the meridian $B_2$ defined by the hemisphere 102. Similar to the angle α described in FIG. 2. Although the specific width of the cutting area 104 is dependent upon the size of the reamer 100 and the area desired to be reamed, the width of the cutting area 104 is generally about 1 mm to about 20 cm. Nevertheless, the cutting surface generally extends at least 90° to about 200° along the meridian $B_2$.

Nevertheless, the hemisphere 102 is substantially continuous, as described further herein. It will be understood that the hemisphere 102 is not necessarily, but may be, a complete hemisphere but substantially hemispherical in shape. For example, the hemisphere 102 may define a portion of the sphere less than a complete half of a sphere.

Defined by the cutting area 104 is a plurality of cutting portions 120. The cutting portions 120 include a cutting edge or cutting face 122, followed by a following edge or surface 124. The cutting face 122 is similar to the cutting edge 18 of the reamer 10. Generally, the cutting edge 122 is able to cut or remove a portion of a biological material, such as a portion of an acetabulum. Adjacent to the cutting edge 122 is a cutting bore or opening 126, which may be partially covered by the following face 124. The opening 126 allows material from the cut surface to be passed into the reamer 100. Specifically, the reamer 100 defines a hollow hemisphere, such that the interior 130 of the reamer 100 is substantially a void. Therefore, the material that is cut from the acetabulum, may be passed through the opening 126 and into the interior 130 of the reamer 100. In this way, as the reamer 100 reams a selected acetabulum, the material is captured and removed from the surface of the acetabulum, such that a cleaner and smoother reaming of the acetabulum may occur. The cutting portions 120 may be provided in any size and number in the cutting area 104 as appropriate. For example, a large number of the cutting portions 120 may completely cover the cutting area 104. Alternatively, a small number of strategically placed cutting portions 120 may be positioned on the cutting area 104.

Similar to the first reamer 10, the second reamer 100 includes an axis of rotation $R_2$ around which the reamer 100 rotates when in operation. The cutting edge 122 defines a leading face or edge of the reamer 100. Therefore, as the reamer 100 rotates around the axis of rotation $R_2$, the cutting edge 122 is the first surface to engage the acetabulum. Thus, the cutting edge may cut a portion of the acetabulum as the reamer 100 rotates around the axis of rotation $R_2$.

As the reamer 100 rotates about the axis $R_2$, the hemisphere 102 substantially stabilizes the reamer 100 within the acetabulum. Specifically, the cutting area 104 defines a portion of the hemisphere 102, such that while the cutting portion 104 is rotated about the axis of rotation $R_2$, a complementary hemisphere is cut within the acetabulum. However, while the cutting area 104 is rotated about the axis of rotation $R_2$, a first stabilization portion 110 and a second stabilization portion 112 help to stabilize the cutting portion 104 within the acetabulum. Specifically, as a hemispherical shape is reamed by the cutting area 104, the stabilization portions 110 and 112 assist in stabilizing the acetabular reamer 100 in a selected axial orientation within the acetabulum. The stabilization portions 110 and 112 complete the hemisphere 102 of the reamer 100, such that the formation of a complementary hemisphere in the acetabulum is easier. That is, the cutting area 104, as it rotates around the axis of rotation $R_2$, cannot easily become unoriented or disoriented with a selected orientation or position within the acetabulum because of the presence of the stabilization portions 110 and 112. Particularly, the axis of rotation $R_2$ can be positioned at a selected point within the acetabulum. Therefore, the stabilization portions 110 and 112 cooperate with the cutting area 104 to ensure that the point selected for the axis of rotation $R_2$ is maintained throughout the reaming procedure.

In this way, the portion reamed is substantially complimentary to the shape of the reamer 100.

In addition, the stabilization portions 110 and 112 provide protection for the soft tissue surrounding the incision or portal formed in the soft tissue to act as the acetabulum. As described further herein, the stabilization portions 110 and 112 assist in moving or pushing the soft tissue away from the cutting area 104 during ingression and egression of the reamer 100.

Extending away from the plane $A_2$ and away from the hemisphere 102 are a first wing or protecting portion 140 and a second wing or protecting portion 142. The edges of the protection wings 140 and 142 are substantially rounded and smooth. The wings 140 and 142 extend a distance from the edge of the hemisphere 102 toward the axis of rotation $R_2$ over the interior 130 of the hemisphere 102. Therefore, the wings 140 and 142 cover at least a portion of the opening of the hemisphere 102 opposite the plane $A_2$ from the hemisphere 102. In addition, the wings 140 and 142 cooperate with the stabilization portions 110 and 112 to form a tissue track. As described further herein, the tissue track assists in moving the soft tissue away from the cutting area 104 during at least egression of the reamer 100. Furthermore, the tissue track assists in moving the soft tissue away from the cutting area 104 during ingression of the reamer 100.

In use, as described further herein, the wings 140 and 142 cooperate with the stabilization portions 110 and 112 to reduce trauma to an incision formed to gain access to the acetabulum. As discussed above, they form the tissue track. Generally, during a procedure to ream the acetabulum, an incision is made in the soft tissue, such that a tool, such as the reamer 100, can be provided adjacent to the acetabulum. To minimize injury or trauma to a patient, the incision is kept to a minimum such as in a minimally invasive procedure. Therefore, the reamer 100 can be inserted through an incision, such that the meridian $B_2$ is substantially aligned with the axis along which the incision is formed. Therefore, the stabilization portions 110 and 112 further separate the incision and provide for an easy access to the acetabulum due to the smooth surface of the stabilization portions 110 and 112. Stabilization portions 110 and 112 generally contain no teeth such that they will not cut or abrade the soft tissue during ingression and egression of the reamer 100.

After the acetabulum has been reamed, the reamer 100 is removed through the incision. The wings 140 and 142 provide a smooth surface, which expands the incision, and any other instruments provided through the incision, for the removal of the reamer 100 from the patient 100. Specifically, the wings 140 and 142 wrap around a portion of the top of the reamer 100, such that they first engage the soft tissue and move it aside as the reamer 100 is pulled from the patient. Therefore, the wings 140 and 142 cooperate with the stabilization portions 110 and 112 to minimize trauma to a patient during a reaming procedure.

The reamer 100 may be operated by any appropriate tool, which will allow for rotational motion around the axis of rotation $R_2$. The tool that can be used, and as described further herein, may engage the reamer 100 in any appropriate manner. For example, the tool may engage the reamer 100 through a tool engaging portion 150. The tool engaging portion 150 generally extends substantially parallel with the meridian $B_2$ defined by the hemisphere 102. Moreover, the tool engaging portion 150 defines an axis substantially perpendicular to the axis of rotation $R_2$. Therefore, an axis of the tool bar $T_2$ allows for ease of rotation around the axis of rotation $R_2$.

The tool engaging bar 150 may define a tool engaging section 152. The tool engaging section 152 may define any appropriate tool engaging recess, such as a square recess 154. The recess 154 may define any appropriate polygonal shape, such as a hexagon or octagon, such that rotational movement of the tool may be easily translated to the tool bar through the tool engaging recess 154. Therefore, as the tool rotates, the tool engages the tool recess 154, which operably interconnects the tool with the reamer 100, such that rotational motion of the tool is translated to the reamer 100. Therefore, the tool may rotate the reamer 100 around the axis of rotation $R_2$, such that the cutting edge 122 of the cutting portions 120 may cut a portion of the acetabulum. Further, during the rotation of the reamer 100 and the cutting by the cutting edge 122, the material is removed from the acetabulum and allowed access to the interior 130 of the reamer 100 through the openings 126 adjacent the cutting edge 122.

With reference to FIGS. 9–12, a reamer 200 according to another alternative embodiment is illustrated. The reamer 200 generally includes a cutting area or section 202. The reamer 200 further includes protection or stabilization portions or bars 204 and 206 extending from the cutting area 202. Extending further from respective protection portions 204 and 206 is a first protection wing or portion 208 and a second protection wing or portion 210. The stabilization portions 204 and 206 cooperate with respective wings 208 and 210 to define a tissue track. As described further herein, the tissue track assists in moving the soft tissue surrounding an incision as the reamer 200 is passed therethrough. Specifically, the tissue track assists in moving the soft tissue away from the cutting section 202 of the reamer 200.

The reamer 200 defines at least a portion of a hemisphere 212 extending above a plane $A_3$. The hemisphere 212 is generally defined by the cutting area 202 and the stabilizing bars 204 and 206. As described further herein, however, the hemisphere 212 is not substantially solid and includes a plurality of openings or voids.

The cutting area 202 extends along a first meridian $B_3$ of the hemisphere 212. The cutting area 202 defines about 1° to about 80° on either side of the meridian $B_3$ of the hemisphere 212 of the reamer 200. Similar to the angle α described in FIG. 2. Therefore, the cutting section 202 does not define an entire hemisphere. Nevertheless, the cutting surface generally extends at least 90° to about 200° along the meridian $B_3$.

Further defined by the cutting area 202 is a plurality of cutting portions 220. The cutting portions 220 generally include a leading or cutting edge 222 and a following face or portion 224. Defined adjacent the cutting edge 222 and generally below the following portion 224 is an opening 226, which allows material to pass through the cutting area 202 into an interior 226 of the reamer 200. That is, the hemisphere 212 of the reamer 200 is substantially hollow and defines a void or open space. In this way, material that is cut or reamed with the reamer 200 can pass through the openings 226 into the interior 212 of the reamer 200 and be captured and removed from the surface of the acetabulum. As described further herein, the material can pass through the cutting area 202 and in through the interior 226 of the reamer 200, such that the cutting of the acetabulum can proceed more efficiently and without obstruction. Furthermore, the material from the acetabulum, which is reamed with the reamer 200, can be easily removed from the acetabulum after it is collected within the interior 226 of the reamer 200. It will be understood that each of the other embodiments may also easily remove material or debris, which is reamed from the acetabulum after it is collected in the interior of the respective reamer.

Each of the cutting edges 222 are formed to allow for cutting of an acetabulum when the reamer 200 is rotated around an axis of rotation $R_3$. That is, the cutting edge 222 is substantially a leading edge of the cutting portion 220 as the reamer 200 rotates in an appropriate direction around the axis of rotation $R_3$. In this way, the cutting edge 222 may cut the selected portion of the acetabulum and the material can be drawn into the interior 226 of the reamer 200.

The stabilizing portions 204 and 206 extend from the cutting section 202 substantially along the surface of the hemisphere 212 defined by the reamer 200. In this way, the stabilizing portions 204 and 206 substantially stabilize the reamer 200 in a selected orientation relative to the acetabulum. That is, the cutting area 202 defines only a portion of the hemisphere 212, substantially defined by the reamer 200. Therefore, the stabilization portions 204 and 206 further define the hemisphere of the reamer 200, such that as the reamer 200 is used to ream a portion of the acetabulum, the reamer 200 is maintained in a substantially stable position. In this way, minor or unintentional movements of a user are not translated to errors in the reaming of the surface of the acetabulum because of the stabilization bars 204 and 206. Specifically, the axis of rotation $R_3$ may be positioned relative to the acetabular in a selected point. The stabilization bars 204 and 206 cooperate with the cutting section 202 to maintain the reamer 200 in the selected orientation such that the axis of rotation $R_3$ remains aligned with the selected point.

Furthermore, the stabilization bars 204 and 206 in conjunction with the cutting area 202 define four quadrants of the hemisphere 212. Furthermore, between the stabilization bars 204 and 206 and the cutting area 202 is defined a first void or window 230, a second void or window 232, a third void or window 234 and a fourth void or window 236. The windows 230–236 are substantially free of material or transparent, such that a user may view an area opposite the viewer through the reamer 200. For example, when the reamer 200 is positioned in an acetabulum, the user would then generally be able to view the acetabulum surface through the reamer 200. However, with the presence of the windows 230–236, the user can view this surface opposite the user through the reamer 200. Furthermore, as the reamer 200 is rotated around the axis of rotation RRR substantially the entire area of the surface being reamed can be viewed through one of the plurality of windows 230–236. In this way, a surface can be reamed substantially completely without removing the reamer 200 from the surface to view the progress of the reaming. This in turn reduces trauma or minimizes trauma to a patient during a procedure.

The windows 230–236 may be substantially devoid of material or include a clear material. For example, a transparent polymer of sufficient hardness and type may be provided in the windows 230–236 to provide for a substantially smooth or continuous surface of the reamer 200. Nevertheless, the transparent material allow for viewing of the acetabular through the reamer 200 such that the reamer 200 may be maintained within the acetabulum substantially during the entire reaming process.

Furthermore, the protection wings 208 and 210, which extend from the stabilization bars 204 and 206, extend over an opening of the interior 226 of the reamer 200. Generally, the edges of the wings 208 and 210 are substantially smooth and minimize trauma as the reamer 200 is inserted or removed from a patient. Moreover, the wings 208 and 210 extend above or away from the hemisphere 212, opposite the plane $A_3$. The wings 208 and 210 extend at least a distance toward the axis of rotation $R_3$. Therefore, the wings 208 and 210 cover a portion of the reamer 200 that would otherwise be exposed if the wings 208 and 210 were not present.

During a procedure, the wings 208 and 210 assist in clearing the path of the reamer 200 of soft tissue or other portions of the anatomy, which can be damaged if abraded by the cutting edges 222. For example, generally during a minimally invasive acetabular reaming, an incision in the soft tissue is kept to a minimum. Therefore, when the reamer 200 is to be removed from the reaming position, the wings 208 and 210 assist in moving apart the soft tissue or other medical instruments, which happen to be present in the incision. Therefore, rather than abrading the soft tissue with the cutting edges 222, the soft tissue is pushed aside with the wings 208 and 210. Moreover, the stabilization bars 204 and 206 further provide a clearing or sweeping of the path of the reamer 200 during the egression of the reamer 200 from the reaming position. Therefore, the stabilization bars 204 and 206 also act as protection members for ingression and egression of the reamer 200. Specifically, the stabilization bars assist in moving the soft tissue away from the cutting section 202 as the reamer 200 is placed into the acetabulum. Furthermore, the stabilization bars 204 and 206 cooperate with the wings 208 and 210 to form a tissue track to move the soft tissue during egression of the reamer 200. Therefore, the stabilization bars 204 and 206 in conjunction with the wings 208 and 210 form a protection section to protect the soft tissue from further trauma due to the ingression and egression of the reamer 200.

The reamer 200 further includes a tool engaging portion 250, which extends along an axis $T_3$ that is substantially perpendicular to the axis of rotation $R_3$. The tool engaging portion 250 substantially interconnects the ends of the cutting area 202 along the plane $A_3$. The tool engaging portion 250 allows any appropriate tool to interconnect with the reamer 200 for reaming of a surface. Generally, as the tool will interconnect with the tool engaging portion 250, such that a rotational motion of the tool may be translated to the reamer 200.

The tool engaging portion 250 may further define a tool engaging section 252, which in turn defines a tool engaging bore 254. The tool engaging bore 254 may be any appropriate shape to allow translation of a rotational motion to the reamer 200. For example, the tool engaging bore 254 may be any appropriate polygonal shape, such as square, octagon, or hexagon. In this way, a complementarily shaped tool can engage the tool engaging bore 254 to allow for rotation of the reamer 200. Therefore, the reamer 200 may cooperate with the tool to provide power to rotate the reamer 200 around the axis of rotation $R_3$. Again, it will be understood that the direction of rotation generally allows the cutting edge 222 to be a leading edge to cut the material within an acetabulum. Nevertheless, it will be understood that it may also be selected to rotate the reamer 200 in a direction away from the cutting edge 222.

Figure 13:
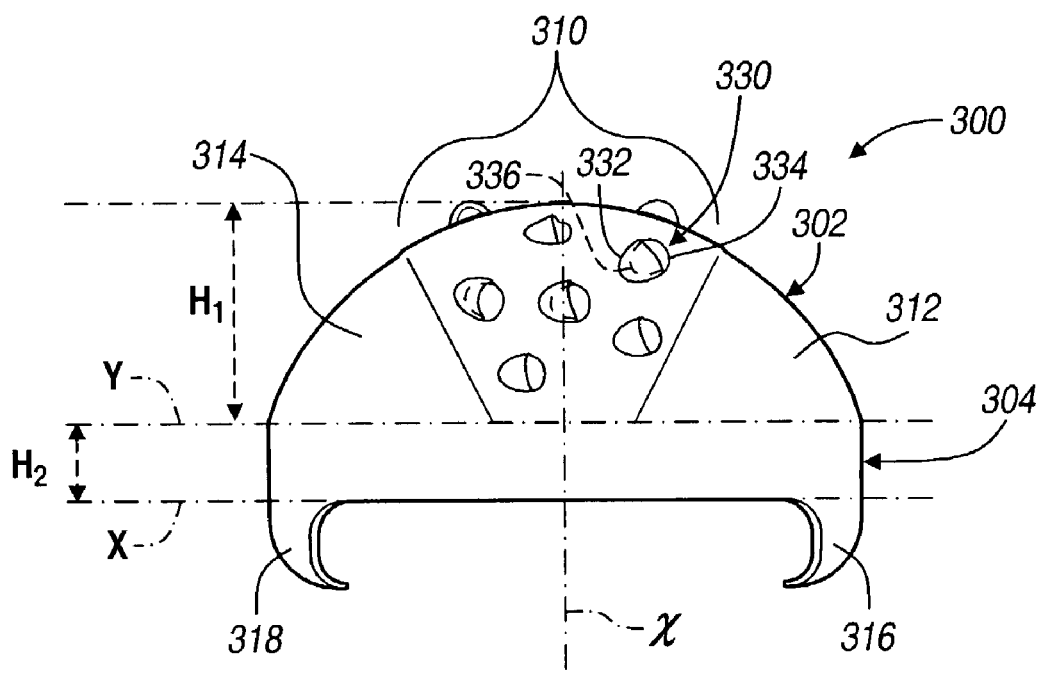
FIG. 13 is a side plan view of a reamer according to a third alternative embodiment.
Figure 14:
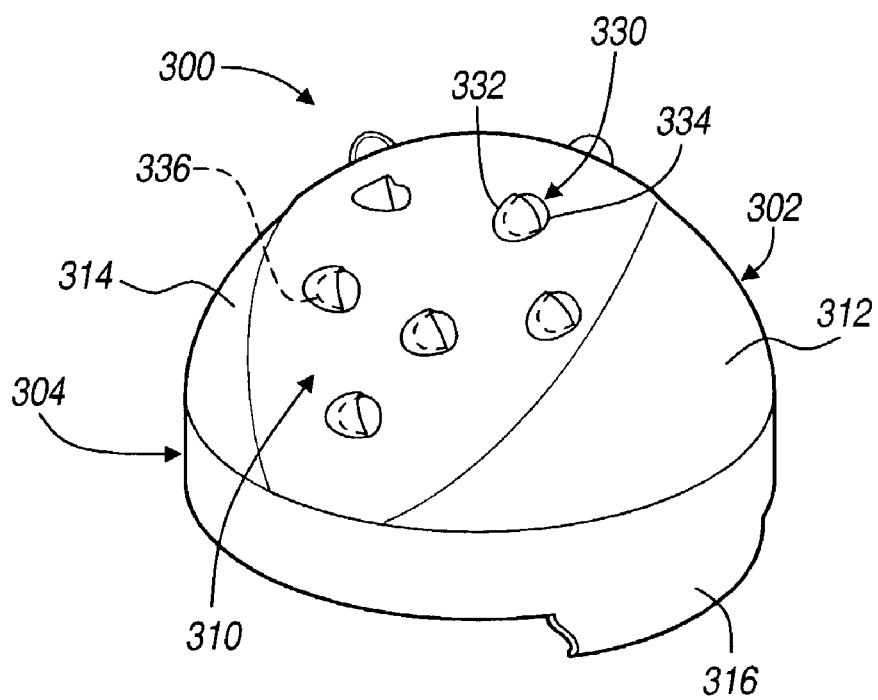
FIG. 14 is a perspective top view of the reamer illustrated in FIG. 13.
Figure 15:
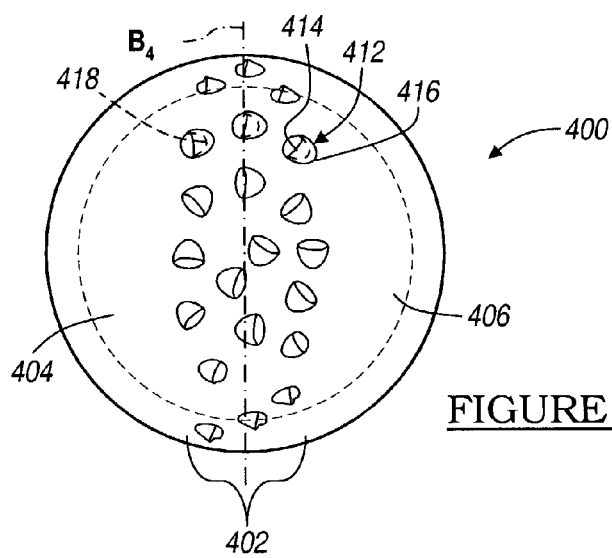
FIG. 15 is a bottom plan view of a reamer according to a further alternative embodiment.
Figure 16:
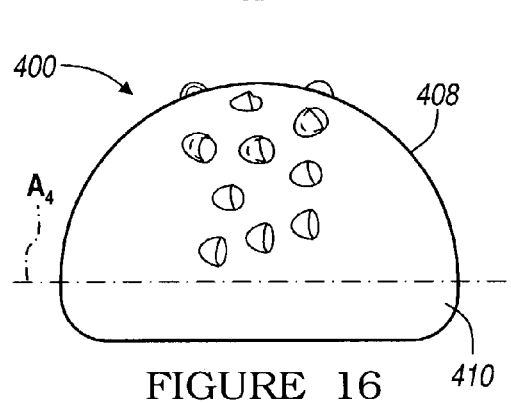
FIG. 16 is a side plan view of a reamer FIG. 15, along the meridian of the scraper teeth.
Figure 17:
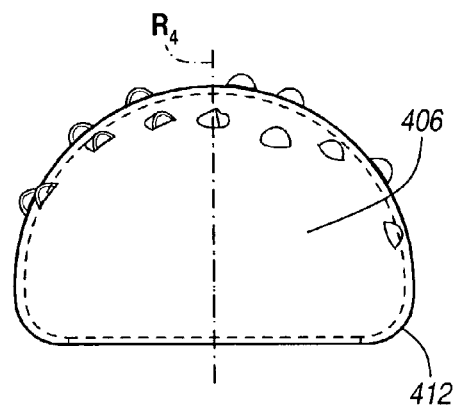
FIG. 17 is a side plan view of the reamer of FIG. 15, along the meridian, which intersects the meridian of the scraper teeth.
Figure 18:
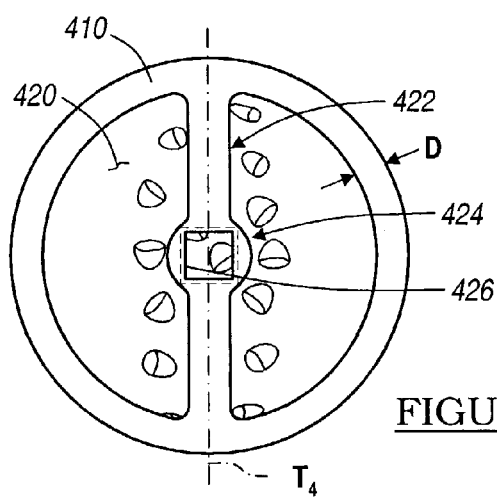
FIG. 18 is a top plan view of the reamer of FIG. 15.
Figure 19:
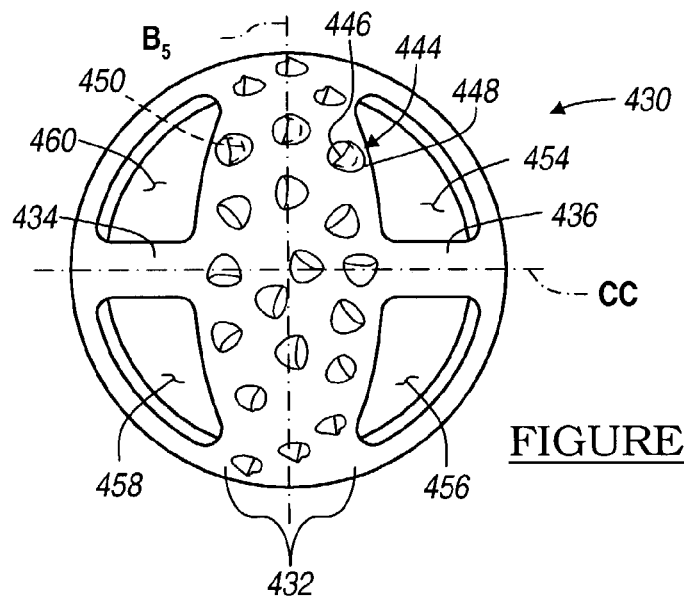
FIG. 19 is a bottom plan view of a reamer according to a further embodiment.
Figure 20:
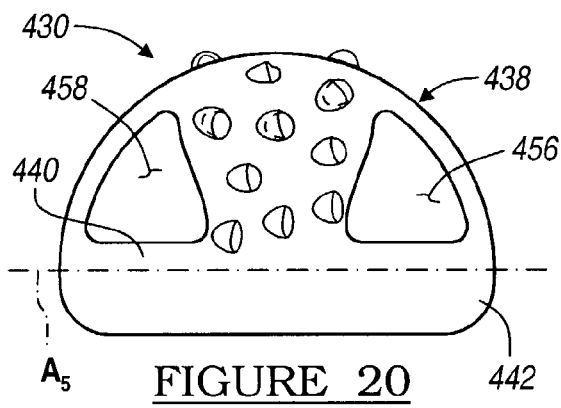
FIG. 20 is a side plan view of the reamer of FIG. 19 along a meridian of the scraper teeth.
Figure 21:
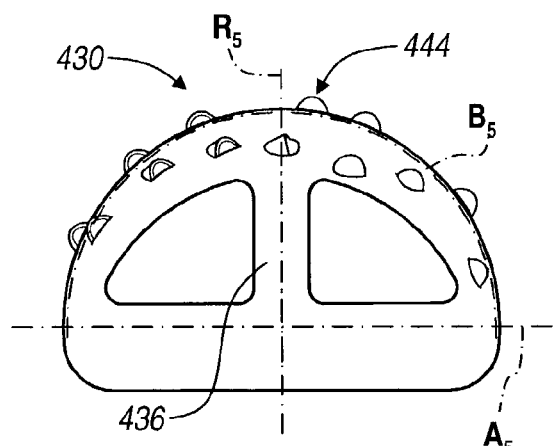
FIG. 21 is a side plan view of the reamer of FIG. 19, along the meridian, which intersects the meridian of the scraper teeth.
Figure 22:
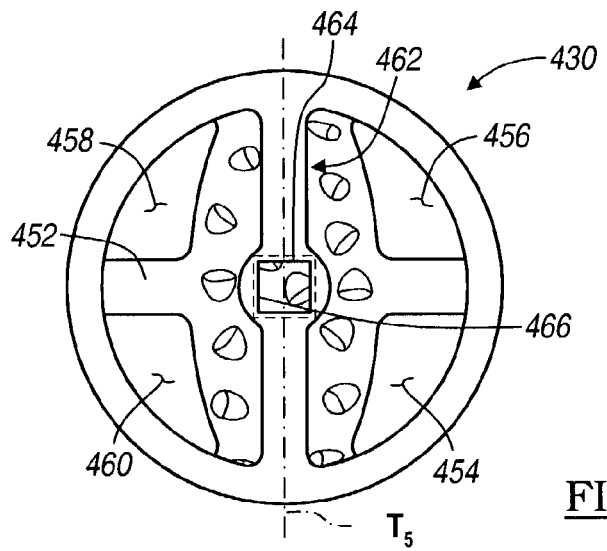
FIG. 22 is a top plan view of the reamer illustrated in FIG. 19.
Figure 23:
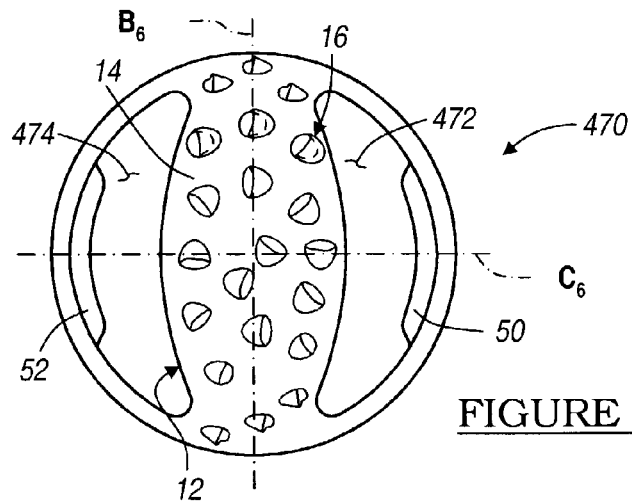
FIG. 23 is a bottom plan view of a reamer according to a further alternative embodiment.
Figure 24:
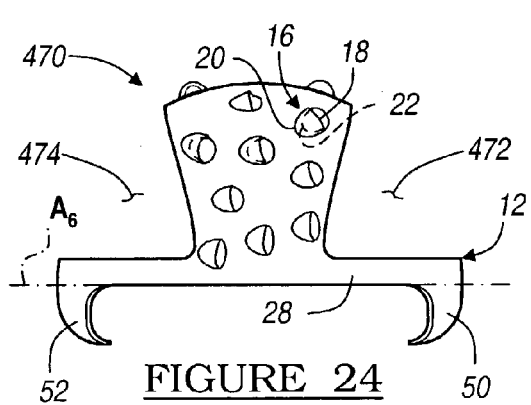
FIG. 24 is a side plan view of a reamer FIG. 23, along the meridian of the scraper teeth.
Figure 25:
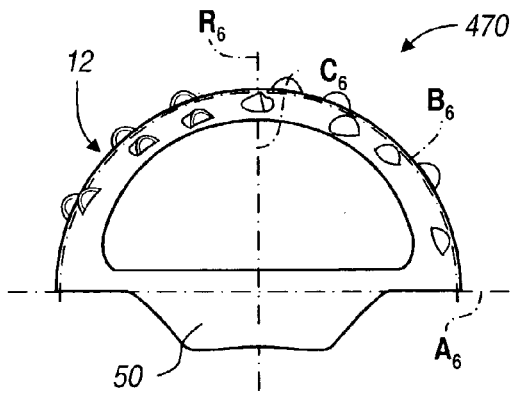
FIG. 25 is a side plan view of the reamer of FIG. 23, along the meridian, which intersects the meridian of the scraper teeth.
Figure 26:
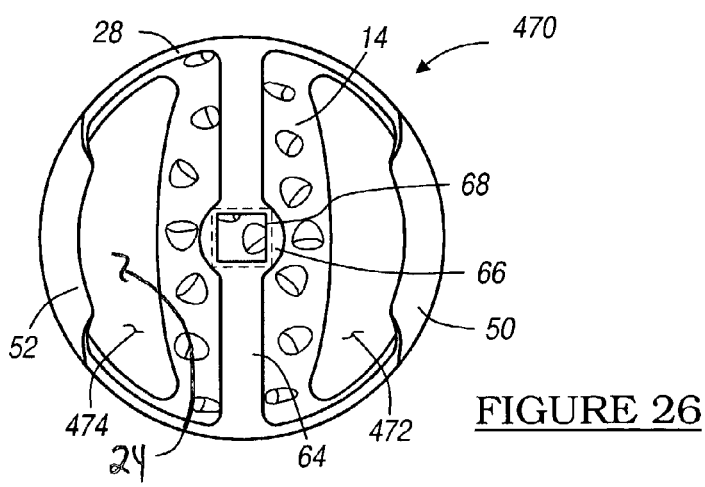
FIG. 26 is a top plan view of the reamer of FIG. 23.
Figure 27:
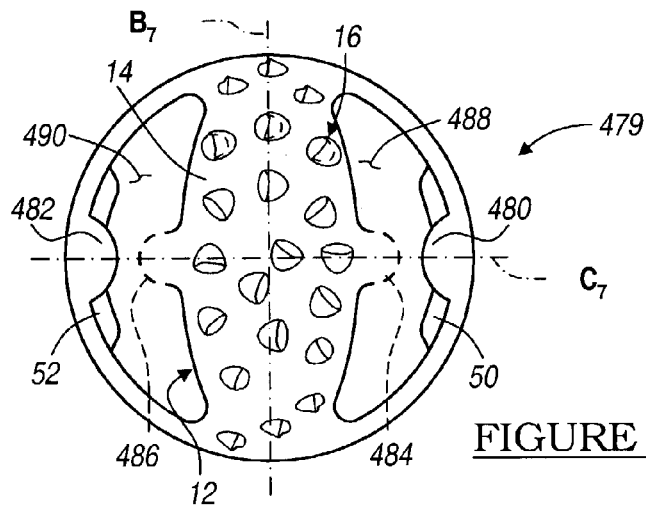
FIG. 27 is a bottom plan view of a reamer according to a further alternative embodiment.
Figure 28:
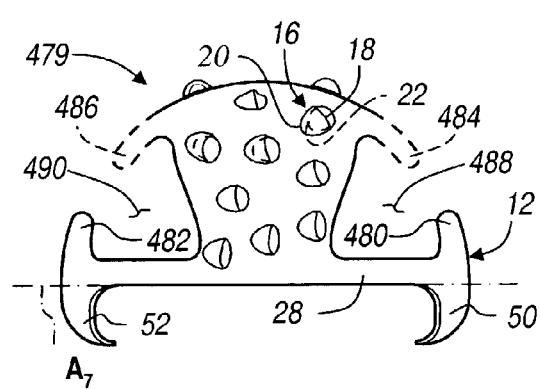
FIG. 28 is a side plan view of a reamer FIG. 27, along the meridian of the scraper teeth.
Figure 29:
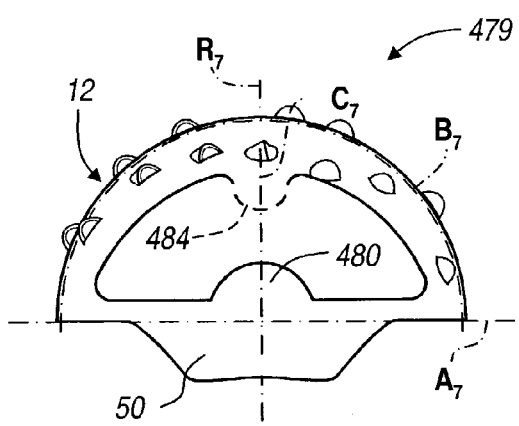
FIG. 29 is a side plan view of the reamer of FIG. 27, along the meridian, which intersects the meridian of the scraper teeth.
Figure 30:
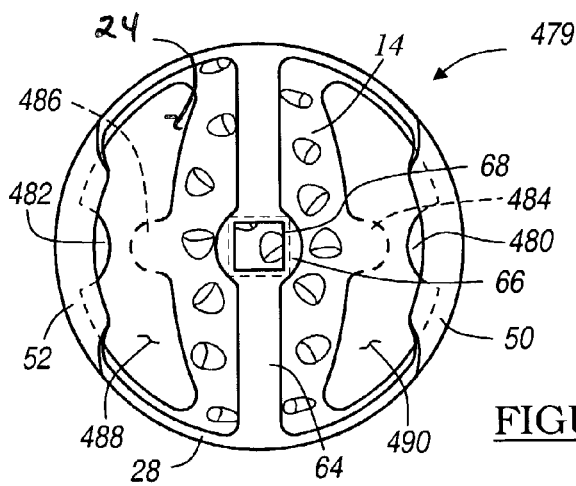
FIG. 30 is a top plan view of the reamer of FIG. 27.

With reference to FIGS. 13 and 14, a reamer 300 according to another alternative embodiment generally defines a hemispherical portion 302 that extends above a first plane X. The reamer further defines a cylindrical portion 304 that extends between the first plane X and a second plane Y. The hemispherical portion 302 defines a cutting area 310 and a first non-cutting or stabilization area 312 and a second non-cutting or stabilization area 314. Therefore, the hemisphere 302 is substantially defined by the cutting area 310 and the two stabilization portions 312 and 314. The cutting area 310 may be any appropriate portion of the hemisphere 302, but generally defines between 1° and 160° of the hemisphere 302. Substantially extending from the cylindrical region 304 in an area adjacent or parallel with the respective stabilization portions 312 and 314 are a first protection portion or wing 316 and a second protection portion or wing 318.

The cutting portion 310 generally defines a plurality of cutting portions 330. The cutting portions 330 include a cutting or leading edge 332 followed by a following or rear face 334. Also, the cutting portions 330 define an opening 336, such that material that is cut by the cutting edge 332 can move through the surface of the reamer 300. Generally, the interior of the hemisphere 302 is substantially hollow, such that a cup or bowl is formed and material may pass through the opening 336 and be collected within the interior of the reamer 300. Therefore, as the reaming of an acetabulum continues, the material that is first reamed can be removed from the surface to allow for ease of additional reaming of the acetabulum. In this way, debris and material is not collected on the surface of the acetabulum, but rather is collected within the interior of the reamer 300. This allows the debris and material to be easily removed from the acetabulum by the reamer 300.

The stabilizing portions 312 and 314 further define the hemisphere 302 of the reamer 300. The stabilizing portions 312 and 314 help in stabilization of the reamer 300 during use, such that the reamer 300 is more easily maintained in a selected orientation within the acetabulum. The cutting area 310 defines only a small portion of the hemisphere 302 of the reamer 300. Therefore, the stabilization portions 312 and 314 assist in maintaining a selected orientation of the reamer 300, rather than providing only the cutting area 310. The complete hemisphere 302 provides for ease of creation of a complementary hemisphere in the acetabulum.

The cutting area 310 substantially defines an axis of rotation Z. That is, the cutting area rotates around the axis of rotation Z such that the cutting edge 332 may cut a portion of the acetabulum. The stabilization portions 312 and 314 assist in holding the axis of rotation Z in a selected orientation. Generally, the axis of rotation may be directed towards or positioned at a selected point in the acetabulum and the stabilization portions 312 and 314 cooperate with the cutting section 310 to assist in holding the axis of rotation Z in the selected orientation or position.

The hemisphere 302 includes a first distance or height $H_1$ of the reamer 300. The cylindrical section 304 includes a second height $H_2$ of the reamer 300. Therefore, the reamer 300 substantially defines a total height of $H_1$ in conjunction with $H_2$. Generally, however, the area to be reamed is substantially equal to the height $H_1$. Therefore, it will be understood that the size of the height $H_1$ may be selected depending upon the size of the area to be reamed by the reamer 300. Moreover, the height $H_2$ of the cylindrical 304 may be selected, depending upon the area to be surrounded by the reamer 300.

The protection wings 316 and 318 extend from the plane Y opposite the cylindrical area 304. Moreover, the wings further extend towards the axis of rotation Z about which the reamer 300 rotates during the reaming procedure. Therefore, the protection wings 316 and 318 cover a portion of the opening of the reamer 300. Generally, this allows for minimization of trauma to a patient during use of the reamer 300.

The wings 316 and 318 cooperate with the stabilization portions 312 and 314 to form a tissue track. The tissue track assists in moving the soft tissue surrounding an incision during ingression and egression of the reamer 300. Specifically, the tissue track assists in moving the soft tissue away from the cutting section 310 during the ingression and egression of the reamer 300. During egression of the reamer, the stabilization portions 312 and 314 assist in first moving the soft tissue away from the cutting section 310 during ingression of the reamer 300. Therefore, trauma to the soft tissue is minimized. Furthermore, during egression of the reamer 300 from the acetabulum, the protection wings 316 and 318 provide for moving the soft tissue and other instruments apart for easy removal of the reamer 300 from the acetabulum.

In addition, the cylindrical area 304 further allows area to be displaced from the cutting area 310 during the beginning and end of the procedure of reaming. Generally, the cylindrical area 304 extends above the reaming area, defined by the hemisphere 302, such that certain soft tissues and instruments can be kept out of the area that is being reamed. Moreover, the cylindrical area 304 further assists in providing an area that moves the soft tissue away from the cutting area 310 that includes the cutting portions 330. It will be understood, that the cylindrical portion 304 may also extend substantially passed the soft tissue from within the patient, such that in the area that is continuously defined that is not covered by the soft tissue. Therefore, the reamer 300 would be able to ream the acetabulum while insuring that soft tissue and other instruments never intersect the area being reamed.

It will be understood that the reamer 300 may include other portions similar to the embodiments discussed above. For example, the reamer 300 may include a tool engaging portion and tool engaging bore. Therefore, the reamer 300 may be used in a similar manner to the various reamer embodiments described above, such that rotational motion of a tool is translated to the reamer 300, such that the reamer 300 is able to rotate around the axis of rotation Z and ream a selected area of an acetabulum.

It will be understood that in various embodiments of a reamer may include transparent regions. That is, regions which allow for viewing of the area opposite the user through the reamer. The transparent regions may either be devoid of a material or include a transparent material, such as a transparent polymer or crystal. Therefore, either complete voids or transparent materials may provide for viewing of an area being reamed, for example an acetabular, without removing the reamer.

With reference to FIGS. 15–18, a reamer 400 according to a further alternative embodiment is illustrated. The reamer 400 generally includes a cutting area or section 402. The reamer 400 further includes protection or stabilization portions or areas 404 and 406 which extend from the cutting area 402. Generally, the cutting area 402 and the stabilization portions 404 and 406 extend from a first claim $A_4$ defining a portion of a sphere 408. The portion of a sphere 408 may be any portion of a sphere generally defines a hemisphere wherein $A_4$ is an equator of the hemisphere 408. Extending on a side of the plane $A_4$ opposite the hemisphere 408 is a protection portion 410. The protection portion 410 generally extends from the plane $A_4$ and towards an axis of rotation $R_4$ of the reamer 400. Therefore the protection portion 410 generally extends a distance D towards an interior or towards the axis of rotation $R_4$ from a periphery of the reamer 400.

The stabilization portions 404 and 406 cooperate with the protective portion 410 to define a tissue track. As described further herein, the tissue track assists in moving the soft tissue surrounding an incision as the reamer 400 is passed therethrough. Specifically, the tissue track assists in moving the soft tissue away from the cutting section 402 of the reamer 400.

The cutting area 402 extends along a first meridian BBBB of the hemisphere 408. The cutting area 402 defines about 1° to about 80° on either side of the meridian $B_4$. Similar to the angle α described in FIG. 2. Generally, the cutting section 402 does not define the entire hemisphere 408. Nevertheless, the cutting section 402 generally extends the entire meridian $B_4$ of the hemisphere 408 to at least about 160°

Further defined by the cutting area 402 is a plurality of cutting portions 412. The cutting portions 412 generally include a leading or cutting edge 414 and a following portion 416. Defined adjacent to the cutting edge 414 and generally below the following portion 416 is an opening 418, which allows material to pass through the cutting area 402 into an interior 420 of the reamer 400. That is, the hemisphere 408 of the reamer 400 is substantially hollow and defines a void or open space. In this way, material that is cut with a reamer 400 can pass through the openings 418 into the interior 420 of reamer 400 to be captured and removed from the surface of the acetabular.

As described further herein, the material can pass through the cutting area 402 and into the interior 420 of the reamer 400 such that the cutting of the acetabulum can proceed more efficiently and without obstruction. Furthermore, the material from the acetabulum, which is reamed with reamer 400, can be easily removed from the acetabulum after it is collected within the interior 420 of the reamer 400.

Each of the cutting edges 414 are formed to allow for cutting of an acetabulum when the reamer 400 is rotated around an axis of rotation $R_4$. That is, the cutting edge 414 is substantially a leading edge of the cutting portion 412 as the reamer 400 rotates in an appropriate direction around the axis of rotation $R_4$. Generally, the reamer 400 reams in a clockwise direction, but it will be understood that it may be designed to ream in a counterclockwise direction. In this way, the cutting edge 412 may cut the selected portion of the acetabulum and the material can be drawn into the interior 420 of the reamer 400.

The stabilizing portions 404 and 406 extend from the cutting section 402 substantially along the surface of the hemisphere 408 defined by the reamer 400. In this way, the stabilizing portions 404 and 406 substantially stabilize the reamer 400 in a selected orientation relative to the acetabulum. That is, the cutting area 402 defines only a portion of the hemisphere 408, substantially defined by the reamer 400. Therefore, the stabilization portions 404 and 406 further define the hemisphere of the reamer 400, such that as the reamer 400 is used to ream a portion of the acetabulum, the reamer 400 is maintained in a substantially stable position. In this way, minor or unintentional movements of a user are not translated to errors in the reaming of the surface of the acetabulum because of the stabilization portions 404 and 406. Specifically, the axis of rotation $R_4$ may be positioned relative to the acetabular in a selected point. The stabilization portions 404 and 406 cooperate with the cutting section 402 to maintain the reamer 400 in the selected orientation such that the axis of rotation RRRR remains aligned with the selected point.

Furthermore, the protection portion 410 that extends from the stabilization portions 404 and 406, extend over an opening of the interior 420 of the reamer 400. Generally, the edges of the portion 410 is substantially smooth and minimize trauma as the reamer 400 is inserted or removed from a patient. Moreover, the protection portion 410 extends above or away from the hemisphere 408, opposite the plane $A_4$. The protection portion 410 extend at least a distance toward the axis of rotation $R_4$. Therefore, the protection portion 410 cover a portion of the reamer 400 that would otherwise be exposed if the protection portion 410 were not present.

During a procedure, the protection portion 410 assist in clearing the path of the reamer 400 of soft tissue or other portions of the anatomy, which can be damaged if abraded by the cutting edges 414. For example, generally during a minimally invasive acetabular reaming, an incision in the soft tissue is kept to a minimum. Therefore, when the reamer 400 is to be removed from the reaming position, the protection portion 410 assist in moving apart the soft tissue or other medical instruments, which happen to be present in the incision. Therefore, rather than abrading the soft tissue with the cutting edges 414, the soft tissue is pushed aside with the protection portion 410. Moreover, the stabilization portions 404 and 406 further provide a clearing or sweeping of the path of the reamer 400 during the egression of the reamer 400 from the reaming position. Therefore, the stabilization portions 404 and 406 also act as protection members for ingression and egression of the reamer 400. Specifically, the stabilization portions 40 and 406 assist in moving the soft tissue away from the cutting section 402 as the reamer 400 is placed into the acetabulum. Furthermore, the stabilization portions 40 and 406 cooperate with the protection portion 410 to form a tissue track to move the soft tissue during egression of the reamer 400. Therefore, the stabilization portions 404 and 406 in conjunction with the protection portion 410 form a protection section or tissue track to protect the soft tissue from further trauma due to the ingression and egression of the reamer 400.

The reamer 400 further includes a tool engaging portion 422, which extends along an axis $T_4$ that is substantially perpendicular to the axis of rotation $R_4$. The tool engaging portion 422 substantially interconnects the ends of the cutting area 402 along the plane $A_4$. The tool engaging portion 422 allows any appropriate tool to interconnect with the reamer 400 for reaming of a surface. Generally, as the tool interconnects with the tool engaging portion 422, such that a rotational motion of the tool may be translated to the reamer 400.

The tool engaging portion 422 may further define a tool engaging section 424, which in turn defines a tool engaging bore 426. The tool engaging bore 426 may be any appropriate shape to allow translation of a rotational motion to the reamer 400. For example, the tool engaging bore 426 may be any appropriate polygonal shape, such as square, octagon, or hexagon. In this way, a complementarily shaped tool can engage the tool engaging bore 426 to allow for rotation of the reamer 400. Therefore, the reamer 400 may cooperate with the tool to provide power to rotate the reamer 400 around the axis of rotation $R_4$. Again, it will be understood that the direction of rotation generally allows the cutting edge 414 to be a leading edge to cut the material within an acetabulum. Nevertheless, it will be understood that it may also be selected to rotate the reamer 400 in a direction away from the cutting edge 414.

With reference to FIGS. 19–22, a reamer 430 according to another alternative embodiment is illustrated. The reamer 400 generally includes a cutting area or section 432. The reamer 430 further includes protection or stabilization portions or bars 434 and 436 extending from the cutting area 432. The cutting section 434 and the stabilization bars 434 and 436 generally define a portion of a sphere 438 extending form a plane $A_5$. The portion of the sphere 438 may be any portion, but generally defines a hemisphere of which $A_5$ is the equator. The cutting section 432 extends along a meridian $B_5$ defined by the hemisphere 438. The cutting section generally extends at least about 170 degrees along meridian $B_5$. Nevertheless, the cutting section generally extends about 1° to about 90° either side of the meridian $B_5$. Similar to the angle α described in FIG. 2. Therefore, the cutting section 432 does not define an entire hemisphere, at least in one direction from meridian $B_5$.

Generally adjacent the plane $A_5$ is a rim 440. Extending from the rim 440 and away from the hemisphere 438 is a protective portion 442. The stabilization portions 434 and 436 cooperate with the protective portion 442 to define a tissue track. As described further herein, the tissue track assists in moving the soft tissue surrounding an incision as the reamer 430 is passed therethrough. Specifically, the tissue track assists in moving the soft tissue away from the cutting section 432 of the reamer 430.

The reamer 430 defines at least a portion of the hemisphere 438 extending above a plane $A_5$. The hemisphere 438 is generally defined by the cutting area 432 and the stabilizing bars 434 and 436. As described further herein, however, the hemisphere 438 is not substantially solid and includes a plurality of openings or voids.

Further defined by the cutting area 432 is a plurality of cutting portions 444. The cutting portions 444 generally include a leading or cutting edge 446 and a following face or portion 448. Defined adjacent the cutting edge 446 and generally below the following portion 448 is an opening 450, which allows material to pass through the cutting area 432 into an interior 452 of the reamer 430. That is, the hemisphere 438 of the reamer 430 is substantially hollow and defines a void or open space. In this way, material that is cut or reamed with the reamer 430 can pass through the openings 450 into the interior 452 of the reamer 430 and be captured and removed from the surface of the acetabulum.

As described further herein, the material can pass through the cutting area 432 and in through the interior 452 of the reamer 430, such that the cutting of the acetabulum can proceed more efficiently and without obstruction. Furthermore, the material from the acetabulum, which is reamed with the reamer 430, can be easily removed from the acetabulum after it is collected within the interior 452 of the reamer 430.

Each of the cutting edges 446 are formed to allow for cutting of an acetabulum when the reamer 430 is rotated around an axis of rotation RRRRR. That is, the cutting edge 449 is substantially a leading edge of the cutting portion 444 as the reamer 430 rotates in an appropriate direction around the axis of rotation $R_5$. In this way, the cutting edge 446 may cut the selected portion of the acetabulum and the material can be drawn into the interior 452 of the reamer 430. Generally, the reamer 430 rotates in a clockwise direction to ream the acetabulum, however, it will be understood that the reamer 430 may rotate in any appropriate direction to ream.

The stabilizing portions 434 and 436 extend from the cutting section 432 substantially along the surface of the hemisphere 438 defined by the reamer 430. In this way, the stabilizing portions 434 and 436 substantially stabilize the reamer 430 in a selected orientation relative to the acetabulum. That is, the cutting area 432 defines only a portion of the hemisphere 438, substantially defined by the reamer 430. Therefore, the stabilization portions 434 and 436 further define the hemisphere of the reamer 434, such that as the reamer 430 is used to ream a portion of the acetabulum, the reamer 430 is maintained in a substantially stable position. In this way, minor or unintentional movements of a user are not translated to errors in the reaming of the surface of the acetabulum because of the stabilization bars 434 and 434. Specifically, the axis of rotation $R_5$ may be positioned relative to the acetabulum in a selected point. The stabilization bars 434 and 436 cooperate with the cutting section 432 to maintain the reamer 430 in the selected orientation such that the axis of rotation RRRRR remains aligned with the selected point.

Furthermore, the stabilization bars 434 and 436 in conjunction with the cutting area 432 define four quadrants of the hemisphere 438. Furthermore, between the stabilization bars 434 and 436 and the cutting area 432, and also within the rim 450, is defined a first viewing area or window 454, a second viewing area or window 456, a third viewing area or window 458, and a fourth viewing area or window 460. The windows 454–460 are substantially free of material or transparent, such that a user may view an area opposite the viewer through the reamer 430. For example, when the reamer 430 is positioned in an acetabulum, the user would then generally be able to view the acetabulum surface through the reamer 430. However, with the presence of the windows 454–460, the user can view this surface opposite the user through the reamer 430. Furthermore, as the reamer 430 is rotated around the axis of rotation RRRRR substantially the entire area of the surface being reamed can be viewed through one of the plurality of windows 454–460. In this way, a surface can be reamed substantially completely without removing the reamer 430 from the surface to view the progress of the reaming. This in turn reduces trauma or minimizes trauma to a patient during a procedure.

The windows 454–460 may be substantially devoid of material or include a clear material. For example, a transparent polymer of sufficient hardness and type may be provided in the windows 454–460 to provide for a substantially smooth or continuous surface of the reamer 430. Nevertheless, the transparent material allow for viewing of the acetabular through the reamer 430 such that the reamer 430 may be maintained within the acetabulum substantially during the entire reaming process.

The protection portion 442 that extends from the rim 440, also extends over an opening of the interior 452 of the reamer 430. Generally, the edges of the protection portion 442 are substantially smooth and minimize trauma as the reamer 430 is inserted or removed from a patient. Moreover, the protection portion 442 extends above or away from the hemisphere 438, opposite the plane $A_5$. The protection portion 442 extends at least a distance toward the axis of rotation $R_5$. Therefore, the protection portion 442 covers a portion of the reamer 430 that would otherwise be exposed if the protection portion 442 were not present.

During a procedure, the protection portion 442 assists in clearing the path of the reamer 430 of soft tissue or other portions of the anatomy, which can be damaged if abraded by the cutting edges 444. For example, generally during a minimally invasive acetabular reaming, an incision in the soft tissue is kept to a minimum. Therefore, when the reamer 430 is to be removed from the reaming position, the protection portion 442 assists in moving apart the soft tissue or other medical instruments, which happen to be present in the incision. Therefore, rather than abrading the soft tissue with the cutting edges 446, the soft tissue is pushed aside with the protection portion 442. Moreover, the stabilization bars 434 and 436 further provide a clearing or sweeping of the path of the reamer 430 during the egression of the reamer 430 from the reaming position. Therefore, the stabilization bars 434 and 436 also act as protection members for ingression and egression of the reamer 430. Specifically, the stabilization bars 434 and 436 assist in moving the soft tissue away from the cutting section 446 as the reamer 430 is placed into the acetabulum.

Furthermore, the stabilization bars 434 and 436 cooperate with the protection portion 442 to form a tissue track to move the soft tissue during egression of the reamer 430. Therefore, the stabilization bars 434 and 436 in conjunction with the protection portion 442 form a protection section or the tissue track to protect the soft tissue from further trauma due to the ingression and egression of the reamer 430.

The reamer 430 further includes a tool engaging portion 462, which extends along an axis $T_5$ that is substantially perpendicular to the axis of rotation $R_5$. The tool engaging portion 462 substantially interconnects the ends of the cutting area 432 along the plane $A_5$. The tool engaging portion 462 allows any appropriate tool to interconnect with the reamer 430 for reaming of a surface. Generally, as the tool will interconnect with the tool engaging portion 462, such that a rotational motion of the tool may be translated to the reamer 430.

The tool engaging portion 462 may further define a tool engaging section 464, which in turn defines a tool engaging bore 466. The tool engaging bore 466 may be any appropriate shape to allow translation of a rotational motion to the reamer 430. For example, the tool engaging bore 466 may be any appropriate polygonal shape, such as square, octagon, or hexagon. In this way, a complementarily shaped tool can engage the tool engaging bore 464 to allow for rotation of the reamer 430. Therefore, the reamer 430 may cooperate with the tool to provide power to rotate the reamer 430 around the axis of rotation $R_5$. Again, it will be understood that the direction of rotation generally allows the cutting edge 446 to be a leading edge to cut the material within an acetabulum. Nevertheless, it will be understood that it may also be selected to rotate the reamer 430 in a direction away from the cutting edge 446.

With reference to FIGS. 23–26, a reamer 470 according to a further alternative embodiment is illustrated. The reamer 470 is similar to the reamer 10 in FIGS. 1–4 and similar numerals are used to call-out similar portions. The reamer 470 generally includes a cutting area or section 14 that defines a portion of the sphere 12. The reamer 470 further includes the rim 28 that also acts as a protection or stabilization portion extending from the cutting area 14 generally adjacent a plane $A_6$. The cutting section 14 defines a portion of the sphere 12 extending from the plane $A_6$. The portion of the sphere 12 may be any portion, but generally defines a hemisphere of which $A_6$ is the equator.

The cutting section 14 extends along a meridian $B_6$ defined by the hemisphere 12. The cutting section generally extends at least about 170 degrees along meridian $B_6$. Nevertheless, the cutting section generally extends about 1° to about 90° either side of the meridian $B_6$. Similar to the angle α described in FIG. 2. Therefore, the cutting section 14 does not define an entire hemisphere, at least in one direction from meridian $B_6$.

Extending from the rim 28 and away from the hemisphere 12 is the first protective portion or wing 50 and the second protective portion or wing 52. The reamer 470 differs from the reamer 10 by not including the additional stabilization portions 26 and 27 to cooperate with the protective portions 50 and 52 to define a tissue track. Nevertheless, the wings 50 and 52 define a tissue track and cooperate with the rim 28 during ingression and egression of the reamer 470. As described further herein, the tissue track assists in moving the soft tissue surrounding an incision as the reamer 470 is passed therethrough. Specifically, the tissue track assists in moving the soft tissue away from the cutting section 14 of the reamer 470.

The reamer 470 defines at least a portion of the hemisphere 12 extending above the plane $A_6$. As described further herein, however, the hemisphere 12 is not substantially solid or includes a plurality of openings or voids.

Further defined by the cutting area 14 are the plurality of cutting portions 16. The cutting portions 16 generally include the leading or cutting edge 18 and the following face or portion 20. It will be understood, however, that the cutting section 14 may include any appropriate cutting portion such as a single or double cutting blade. Defined adjacent the cutting edge 18 and generally below the following portion 20 is an opening 22, which allows material to pass through the cutting area 14 into the interior 24 of the reamer 470. That is, the hemisphere 12 of the reamer 470 is substantially hollow and defines a void or open space. In this way, material that is cut or reamed with the reamer 470 can pass through the openings 22 into the interior 24 of the reamer 470 and be captured and removed from the surface of the acetabulum.

As described further herein, the material can pass through the cutting area 14 and in through the interior 24 of the reamer 470, such that the cutting of the acetabulum can proceed more efficiently and without obstruction. Furthermore, the material from the acetabulum, which is reamed with the reamer 470, can be easily removed from the acetabulum after it is collected within the interior 24 of the reamer 470.

Each of the cutting edges 18 are formed to allow for cutting of an acetabulum when the reamer 470 is rotated around an axis of rotation $R_6$. That is, the cutting edge 18 is substantially a leading edge of the cutting portion 16 as the reamer 470 rotates in an appropriate direction around the axis of rotation $R_6$. In this way, the cutting edge 18 may cut the selected portion of the acetabulum and the material can be drawn into the interior 24 of the reamer 470. Generally, the reamer 470 rotates in a clockwise direction to ream the acetabulum, however, it will be understood that the reamer 470 may rotate in any appropriate direction to ream.

The stabilizing portion or rim 28 extends from the cutting section 14 substantially along the plane $A_6$. In this way, the stabilizing portion 28 assist in stabilizing the reamer 470 in a selected orientation relative to the acetabulum. That is, the cutting area 14 defines only a portion of the hemisphere 12, substantially defined by the reamer 470. The stabilizing portion 28 assists in orienting the reamer 470 during use. In this way, minor or unintentional movements of a user are not translated to errors in the reaming of the surface of the acetabulum because of the stabilization portion 28. Specifically, the axis of rotation $R_6$ may be positioned relative to the acetabulum in a selected point. The stabilization portion 28 cooperates with the cutting section 14 to maintain the reamer 470 in the selected orientation such that the axis of rotation $R_6$ remains aligned with the selected point.

Furthermore, the cutting area 14 defines two portions of the hemisphere 12. Specifically, between the cutting area 14 and within the rim 28, is defined a first viewing area or window 472 and a second viewing area or window 474. The windows 472 and 474 are substantially free of material or are transparent, such that a user may view an area opposite the viewer through the reamer 470. For example, when the reamer 470 is positioned in an acetabulum, the user would then generally be able to view the acetabulum surface through the reamer 470. The presence of the windows 472 and 474 allow the user to view this surface opposite the user through the reamer 470. Furthermore, as the reamer 470 is rotated around the axis of rotation $R_6$ substantially the entire area of the surface being reamed can be viewed through one of the plurality of windows 474 and 474. In this way, a surface can be reamed substantially completely without removing the reamer 470 from the surface to view the progress of the reaming. This in turn reduces trauma or minimizes trauma to a patient during a procedure.

The windows 472 and 474 may be substantially devoid of material or include a clear material. For example, a transparent polymer of sufficient hardness and type may be provided in the windows 472 and 474 to provide for a substantially smooth or continuous surface of the reamer 470. Nevertheless, the transparent material allows for viewing of the acetabulum through the reamer 470 such that the reamer 470 may be maintained within the acetabulum substantially during the entire reaming process.

The protection portions 50 and 52 that extend from the rim 28, also extend over an opening of the interior 24 of the reamer 470. Generally, the edges of the protection portions 50 and 52 are substantially smooth and minimize trauma as the reamer 470 is inserted or removed from a patient. Moreover, the protection portions 50 and 52 extend above or away from the hemisphere 12, opposite the plane $A_6$. The protection portions 50 and 52 extend at least a distance toward the axis of rotation $R_6$. Therefore, the protection portions 50 and 52 cover a portion of the reamer 470 that would otherwise be exposed if the protection portions 50 and 52 were not present.

During a procedure, the protection portions 50 and 52 assist in clearing the path of the reamer 470 of soft tissue or other portions of the anatomy, which can be damaged if abraded by the cutting edges 18. For example, generally during a minimally invasive acetabular reaming, an incision in the soft tissue is kept to a minimum. Therefore, when the reamer 470 is to be removed from the reaming position, the protection portions 50 and 52 assist in moving apart the soft tissue or other medical instruments, which happen to be present in the incision. Therefore, rather than abrading the soft tissue with the cutting edges 18, the soft tissue is pushed aside with the protection portions 50 and 52. Moreover, the stabilization portion 28 further provides a clearing or sweeping of the path of the reamer 470 during the egression of the reamer 470 from the reaming position. Therefore, the stabilization portion 28 may also act as a protection member for ingression and egression of the reamer 470.

The reamer 470 further includes the tool engaging portion 64, which extends along an axis $T_6$ that is substantially perpendicular to the axis of rotation $R_6$. The tool engaging portion 64 substantially interconnects the ends of the cutting area 14 along the plane $A_6$. The tool engaging portion 64 allows any appropriate tool to interconnect with the reamer 470 for reaming of a surface. Generally, as the tool will interconnect with the tool engaging portion 64, such that a rotational motion of the tool may be translated to the reamer 470.

The tool engaging portion 64 may further define a tool engaging section 66, which in turn defines a tool engaging bore 68. The tool engaging bore 68 may be any appropriate shape to allow translation of a rotational motion to the reamer 470. For example, the tool engaging bore 68 may be any appropriate polygonal shape, such as square, octagon, or hexagon. In this way, a complementarily shaped tool can engage the tool engaging bore 68 to allow for rotation of the reamer 470. Therefore, the reamer 470 may cooperate with the tool to provide power to rotate the reamer 470 around the axis of rotation $R_6$. Again, it will be understood that the direction of rotation generally allows the cutting edge 18 to be a leading edge to cut the material within an acetabulum.

Nevertheless, it will be understood that it may also be selected to rotate the reamer 470 in a direction away from the cutting edge 18.

With reference to FIGS. 27–30, a reamer 479 according to a further alternative embodiment is illustrated. The reamer 479 is similar to the reamer 10 in FIGS. 1–4 and similar numerals are used to call-out similar portions. The reamer 479 generally includes a cutting area or section 14 that defines a portion of the sphere 12. The reamer 479 further includes the rim 28 that also acts as a protection or stabilization portion extending from the cutting area 14 generally adjacent a plane $A_7$. The cutting section 14 defines a portion of the sphere 12 extending form the plane $A_7$. The portion of the sphere 12 may be any portion, but generally defines a hemisphere of which $A_7$ is the equator.

The cutting section 14 extends along a meridian $B_7$ defined by the hemisphere 12. The cutting section generally extends at least about 170 degrees along meridian $B_7$. Nevertheless, the cutting section generally extends about 1° to about 90° either side of the meridian $B_7$. Similar to the angle $\alpha$ described in FIG. 2. Therefore, the cutting section 14 does not define an entire hemisphere, at least in one direction from meridian $B_7$.

Extending from the rim 28 and away from the hemisphere 12 is the first protective portion or wing 50 and the second protective portion or wing 52. The reamer 479 differs from the reamer 10 by not including the additional stabilization portions 26 and 27 to cooperate with the protective portions 50 and 52 to define a tissue track. Nevertheless the reamer 479 includes a first protection portion or barb 480 and a second protection portion or barb 482. The barbs 480 and 482 extend generally along axis $C_7$ in the same direction relative to the plane $A_7$ as the sphere portion 12. In the alternative or in addition to the first and second barbs 480 and 482 a third barb 484 and a fourth barb 486 (both shown in phantom) may be included.

The wings 50 and 52 alone or in combination with the barbs 480 and 482 define a tissue track and cooperate with the rim 28 during ingression and egression of the reamer 479. As described further herein, the tissue track assists in moving the soft tissue surrounding an incision as the reamer 479 is passed therethrough. Specifically, the tissue track assists in moving the soft tissue away from the cutting section 14 of the reamer 479.

The reamer 479 defines at least a portion of the hemisphere 12 extending above the plane $A_7$. As described further herein, however, the hemisphere 12 is not substantially solid or includes a plurality of openings or voids.

Further defined by the cutting area 14 are the plurality of cutting portions 16. The cutting portions 16 generally include the leading or cutting edge 18 and the following face or portion 20. It will be understood, however, that the cutting section 14 may include any appropriate cutting portion such as a single or double cutting blade. Defined adjacent the cutting edge 18 and generally below the following portion 20 is an opening 22, which allows material to pass through the cutting area 14 into the interior 24 of the reamer 479. That is, the hemisphere 12 of the reamer 479 is substantially hollow and defines a void or open space. In this way, material that is cut or reamed with the reamer 479 can pass through the openings 22 into the interior 24 of the reamer 479 and be captured and removed from the surface of the acetabulum.

As described further herein, the material can pass through the cutting area 14 and in through the interior 24 of the reamer 479, such that the cutting of the acetabulum can proceed more efficiently and without obstruction. Furthermore, the material from the acetabulum, which is reamed with the reamer 479, can be easily removed from the acetabulum after it is collected within the interior 24 of the reamer 479.

Each of the cutting edges 18 are formed to allow for cutting of an acetabulum when the reamer 479 is rotated around an axis of rotation $R_7$. That is, the cutting edge 18 is substantially a leading edge of the cutting portion 16 as the reamer 479 rotates in an appropriate direction around the axis of rotation $R_7$. In this way, the cutting edge 18 may cut the selected portion of the acetabulum and the material can be drawn into the interior 24 of the reamer 479. Generally, the reamer 479 rotates in a clockwise direction to ream the acetabulum, however, it will be understood that the reamer 479 may rotate in any appropriate direction to ream.

The stabilizing portion or rim 28 extends from the cutting section 14 substantially along the plane $A_7$. In this way, the stabilizing portion 28 assists in stabilizing the reamer 479 in a selected orientation relative to the acetabulum. The barbs 480 and 482 may also assist in stabilizing the reamer 479. The stabilizing portion 28 and the barbs 480 and 482 assist in orienting the reamer 479 during use. In this way, minor or unintentional movements of a user are not translated to errors in the reaming of the surface of the acetabulum because of the stabilization portion 28 and barbs 480 and 482. Specifically, the axis of rotation $R_7$ may be positioned relative to the acetabulum in a selected point. The stabilization portion 28 and barbs 480 and 482 cooperate with the cutting section 14 to maintain the reamer 479 in the selected orientation such that the axis of rotation $R_7$ remains aligned with the selected point.

Furthermore, the cutting area 14 defines two portions of the hemisphere 12. Specifically, between the cutting area 14 and within the rim 28, is defined a first viewing area or window 488 and a second viewing area or window 490. The windows 488 and 490 are substantially free of material or are transparent, such that a user may view an area opposite the viewer through the reamer 479. For example, when the reamer 479 is positioned in an acetabulum, the user would then generally be able to view the acetabulum surface through the reamer 479. The presence of the windows 488 and 490 allow the user to view this surface opposite the user through the reamer 479. Furthermore, as the reamer 479 is rotated around the axis of rotation $R_7$ substantially the entire area of the surface being reamed can be viewed through one of the plurality of windows 488 and 490. In this way, a surface can be reamed substantially completely without removing the reamer 479 from the surface to view the progress of the reaming. This in turn reduces trauma or minimizes trauma to a patient during a procedure.

The windows 488 and 490 may be substantially devoid of material or include a clear material. For example, a transparent polymer of sufficient hardness and type may be provided in the windows 488 and 490 to provide for a substantially smooth or continuous surface of the reamer 479. Nevertheless, the transparent material allows for viewing of the acetabulum through the reamer 479 such that the reamer 479 may be maintained within the acetabulum substantially during the entire reaming process.

The protection portions 50 and 52 that extend from the rim 28 also extend over an opening of the interior 24 of the reamer 479. Generally, the edges of the protection portions 50 and 52 are substantially smooth and minimize trauma as the reamer 479 is inserted or removed from a patient. Moreover, the protection portions 50 and 52 extend above or away from the hemisphere 12, opposite the plane $A_7$. The protection portions 50 and 52 extend at least a distance toward the axis of rotation $R_7$. Therefore, the protection portions 50 and 52 cover a portion of the reamer 479 that would otherwise be exposed if the protection portions 50 and 52 were not present.

Furthermore, the barbs 480 and 482 cooperate with the protection portions 50 and 53 to form a tissue track to move the soft tissue during egression of the reamer 479. Therefore, the barbs 480 and 482 in conjunction with the protection portions 50 and 52 form a protection section or the tissue track to protect the soft tissue from further trauma due to the ingression and egression of the reamer 479.

During a procedure, the protection portions 50 and 52 assist in clearing the path of the reamer 479 of soft tissue or other portions of the anatomy, which can be damaged if abraded by the cutting edges 18. For example, generally during a minimally invasive acetabular reaming, an incision in the soft tissue is kept to a minimum. Therefore, when the reamer 479 is to be removed from the reaming position, the protection portions 50 and 52 assist in moving apart the soft tissue or other medical instruments, which happen to be present in the incision. Therefore, rather than abrading the soft tissue with the cutting edges 18, the soft tissue is pushed aside with the protection portions 50 and 52. Moreover, the stabilization portion 28 further provides a clearing or sweeping of the path of the reamer 479 during the egression of the reamer 479 from the reaming position. Therefore, the stabilization portion 28 may also act as a protection member for ingression and egression of the reamer 479.

The reamer 479 further includes the tool engaging portion 64, which extends along an axis $T_7$ that is substantially perpendicular to the axis of rotation $R_7$. The tool engaging portion 64 substantially interconnects the ends of the cutting area 14 along the plane $A_7$. The tool engaging portion 64 allows any appropriate tool to interconnect with the reamer 479 for reaming of a surface. Generally, as the tool will interconnect with the tool engaging portion 64, such that a rotational motion of the tool may be translated to the reamer 479.

The tool engaging portion 64 may further define a tool engaging section 66, which in turn defines a tool engaging bore 68. The tool engaging bore 68 may be any appropriate shape to allow translation of a rotational motion to the reamer 479. For example, the tool engaging bore 68 may be any appropriate polygonal shape, such as square, octagon, or hexagon. In this way, a complementarily shaped tool can engage the tool engaging bore 68 to allow for rotation of the reamer 479. Therefore, the reamer 479 may cooperate with the tool to provide power to rotate the reamer 479 around the axis of rotation $R_7$. Again, it will be understood that the direction of rotation generally allows the cutting edge 18 to be a leading edge to cut the material within an acetabulum. Nevertheless, it will be understood that it may also be selected to rotate the reamer 479 in a direction away from the cutting edge 18.

It will be understood that the above described embodiments are merely exemplary embodiments of a reamer according to the present description and following claims. The following, will also be understood, to merely be an exemplary method of use of a reamer according to the present description. Therefore, the following description will be understood to be merely exemplary in nature and not limiting the following claims. Moreover, although the method described herein will be specifically discussed in conjunction with the reamer 10 according to the first embodiment will be understood that with the various differing portions of the other various embodiments may be used in a similar manner.

Figure 31:
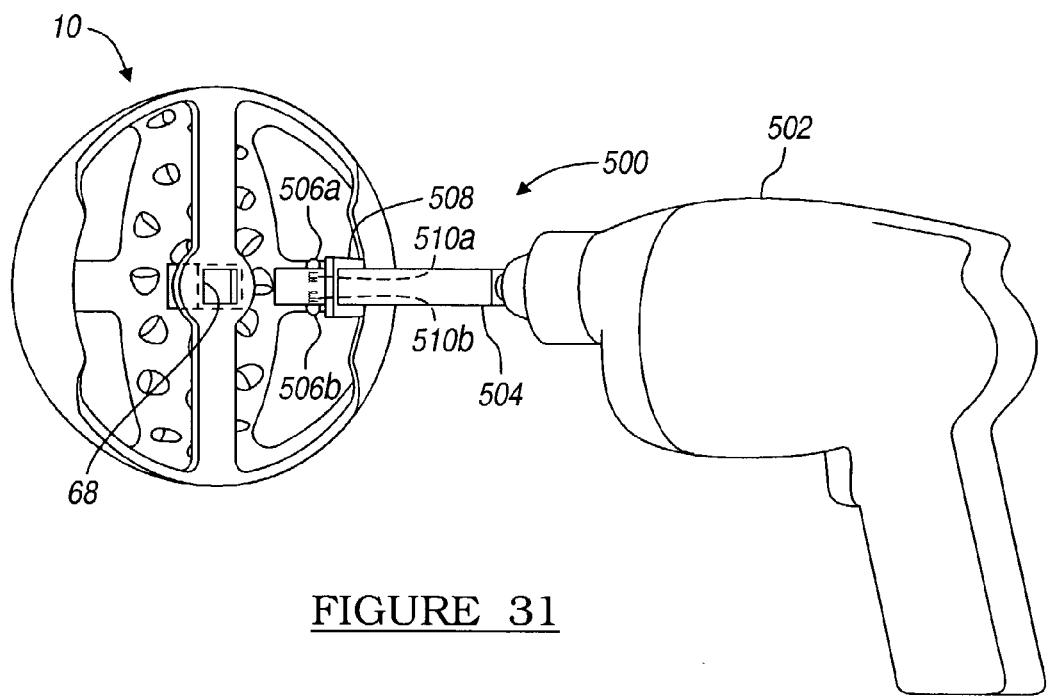
FIG. 31 is a detail view of a tool exploded from the reamer.
Figure 31A:
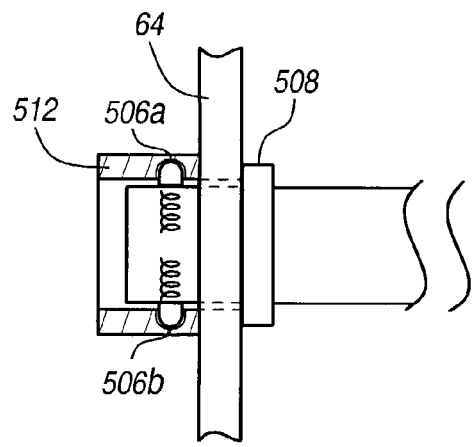
FIG. 31A is a detail partial cross-sectional view of the tool engaging the reamer.

With reference to FIGS. 31 and 13A, the reamer 10 may be interconnected with a tool 500. The tool 500 generally includes a motor portion 502 and an engaging portion 504. The engaging portion 504 of the tool 500 generally includes a shape complementary to the tool engaging bore 68 of the reamer 10. For example, the tool engaging bore 68 is substantially square in cross-section. Therefore, the engaging portion 504 also includes a substantially square cross-section to engage the tool engaging bore 68.

The tool 500 may include any appropriate means to engage the reamer 10 for reaming of an acetabulum. For example, the tool 500 may include a first set of depressible bearings 506a and 506b. Further, the tool 500 includes a second fixed ring or lip 508. Therefore, the engaging portion 504 may be pressed against the tool engaging member 64 of the reamer 10 through the tool engaging bore 68. As this occurs, the depressible bearings 506a and 506b compress springs 510a and 510b, such that the bearings 506a and 506b are pressed into the engaging portion 504. This allows the engaging portion 504 to pass through the tool engaging bore 68, such that at least a portion of the engaging portion 504 passes through the tool engaging bore 68. A wall or socket 512 may also be included that extends from the tool engaging member 64 and adjacent the tool engaging bore 68. The bearings 506a and 506b may engage a portion of the wall 512 or a depression formed therein. Alternatively, the tool 500 may not include the bearings and only engage the wall 512.

Once the depressible bearings 506a and 506b have passed through the tool engaging bore 68, the respective springs 510a and 510b are no longer compressed, therefore, allowing the depressible bearings 506a and 506b to be pushed outward and engage the underside of the tool engaging member 64. The fixed ring 508 stops further displacement of the reamer engaging portion 504 into the reamer 10. Therefore, the tool 500 is held in place by the fixed ring 508 on one side of the tool engaging member 64 and the depressible bearings 506a and 506b on the second side of the tool engaging member 64. In this way, the reamer 10 is interconnected with the tool 500, such that rotational movement of the engaging portion 504 allow for rotational movement of the reamer 10 during use. It will be understood, however, that any appropriate interconnection portion may be provided between the tool 500 and the reamer 10.

Figure 32:
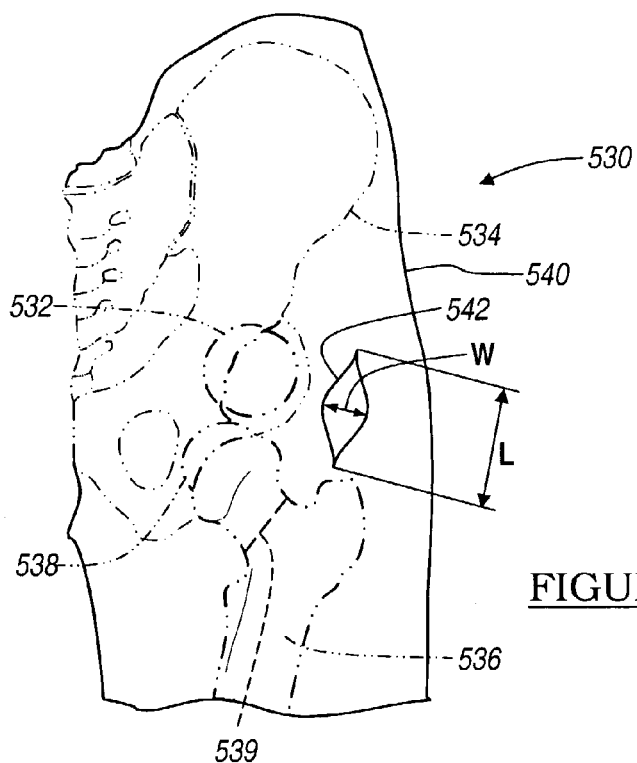
FIG. 32 is a detail view of a portion of a human anatomy.

With reference to FIG. 32, the reamer 10 is generally used to ream a portion of anatomy of a patient 530. Generally, the reamer 10 is used to ream a portion of an acetabulum 532, which is defined by a pelvis 534 of the patient 530. Generally, a femur 536 includes a femoral head 538 that articulates with the acetabulum 532. However, to ream the acetabulum 532 a portal 542 must be formed in a soft tissue 540, generally including at least muscle, adipose, and dermi. The portal 542 must be provided through the soft tissue 540 to allow for the introduction of the reamer 10 to the acetabulum 532. Therefore, the incision or portal 542 is made in the soft tissue 540 at an appropriate position relative to the acetabulum 532. The incision 542 generally extends along an axis and has a length of L. The length L of the incision 542 can be any appropriate length, but is generally about three centimeters to about thirty centimeters. Nevertheless, the use of the reamers as described herein allows the length L of the incision 542 to generally be less than about ten centimeters. It will be understood, however, that incisions of even lesser or greater lengths may be provided depending upon the particular shape and size of the selected reamer and the individual patient. Also the length L may be selected depending upon the size of the implant. To gain access to the acetabular 532, either before or after the incision 542 is formed in the soft tissue 540, the femoral head 538 is generally dislocated from the acetabulum 532 or resected along line 539 from the femur 536.

Figure 33:
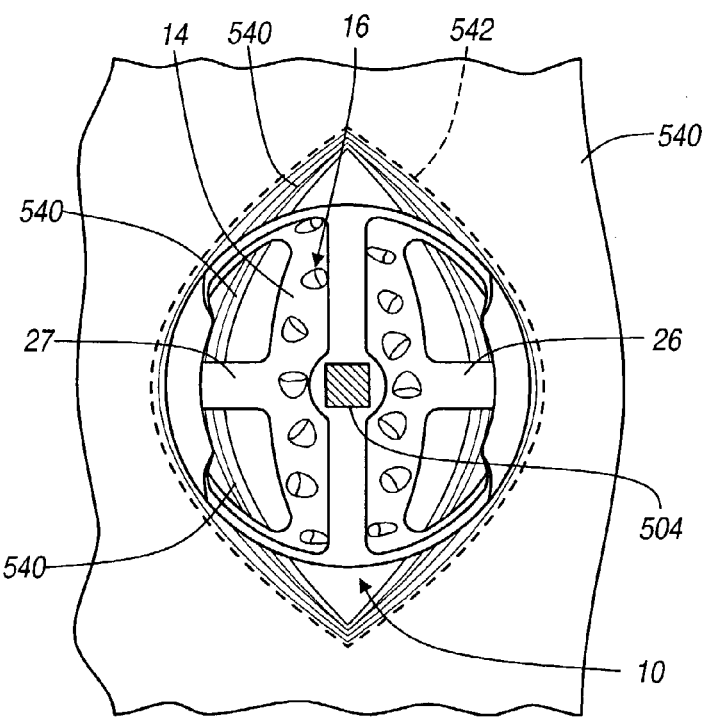
FIG. 33 is a detail view of an incision with a reamer passing therethrough.

With continuing reference to FIG. 32 and additional reference to FIG. 33, the reamer 10 can be pressed through the incision 542, even though the incision 542 is substantially small. Generally, a width W of the incision unstretched, is less than a diameter of the reamer 10. The stabilization bars 26 and 27 define at least a portion of the tissue track to push or dislocate the soft tissue 540 defining the incision 542, such that the cutting area 14 does not engage the soft tissue 540 defining the incision 542. Because the cutting area 14 defines the plurality of cutting portions 16 and the stabilization portions 26 and 27 are substantially smooth, if the cutting area 14 does not engage the soft tissue 540 defining the incision 542 substantially no additional trauma occurs to the soft tissue defining the incision 542. In this way, the use of the reamer 10 may substantially minimize trauma to the incision 542 beyond the incision made. When the incision 542 is minimally traumatized, rehabilitation of the incision 542 is simplified and shortened. For example, when a clean or untraumatized edge is defined, it may more easily accept sutures, staples, or surgical adhesives, such that an ease of closing the incision 542 is provided. In addition, bleeding and other traumatic injuries may be reduced by insuring that none of the cutting portions 16 on the cutting surface 14 engage the soft tissue 540.

After the reamer 10 has been passed through the incision 542, the reaming of the acetabulum 532 may proceed. Therefore, rotation of the tool 500 rotates the reamer 10, such that the acetabulum 532 can be reamed by the cutting portion 516 defined by the cutting area 14. It will be understood that any of the above described reamers may be used to pass the reamer through the incision 542 The portions described in conjunction with each of various embodiments provide for protection of the soft tissue 540 defining the incision 542, such that trauma to the soft tissue 540 may be minimized.

In addition, with specific reference to the third alternative embodiment reamer 300, illustrated in FIGS. 13 and 14, the cylindrical portion 304 may further extend from the reamer 300, after it is inserted into the acetabulum, substantially adjacent to or beyond the soft tissue 540 to the exterior of the patient 530. Therefore, substantially, no soft tissue intersects the area being reamed by the reamer 300 if that reamer is being used.

Figure 34:
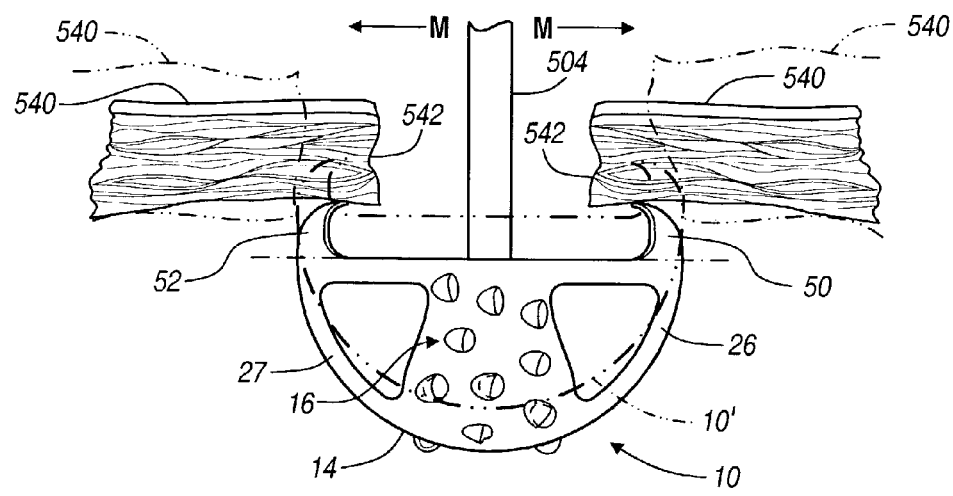
FIG. 34 is a side detail view of the reamer being removed from an incision.
Figure 35:
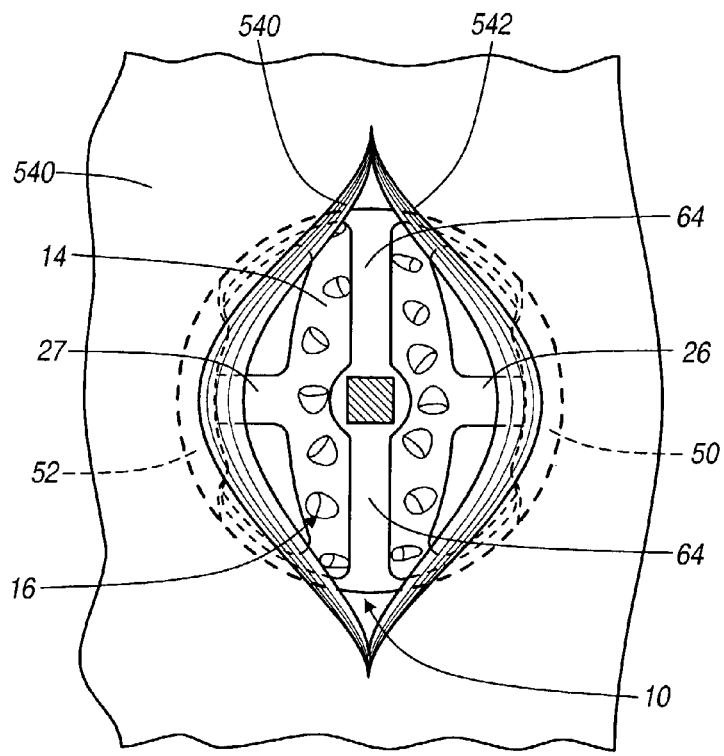
FIG. 35 is a top view of the reamer being removed from an incision.

With reference to FIGS. 34 and 35, after the procedure of reaming the acetabulum 532 is complete, the reamer 10 is removed from the acetabulum and further from the patient. To remove the reamer 10 from the patient, the reamer 10 must be again passed through the incision 542 in a direction opposite the direction required for the insertion of the reamer 10. Generally, because of the incision 542 is selected to be a minimally invasive incision, the incision 542 may substantially close around at least a portion of the reamer engaging portion 504. Therefore, the soft tissue 540 may overlap at least a portion of the reamer 10 after the reamer 10 has been inserted into the patient 530. Therefore, a portion of the soft tissue 540 must either be removed or displaced to remove the reamer 10 from the patient 530 after the reaming procedure has been completed.

The tissue track may give assistance in moving the soft tissue 540 such that it does not engage the cutting section 14 of the reamer 10. Specifically, the protection wings 50 and 52 first abut the soft tissue 540 to again move the soft tissue 540 aside around the incision 542. As the reamer 10 is pulled out from the acetabulum, the wings 50 and 52 move the soft tissue a distance such that the reamer 10 may be easily removed from the patient via the incision 542. As described further herein, the wings 50 and 52 cooperate with the stabilization bars 26 and 27 to provide the soft tissue track to allow for easy removal of the reamer 10 and substantially minimize abrasion of the soft tissue 540 by the cutting edges 18.

The protective wings 50 and 52 engage an interior portion of the soft tissue 540 and begin to move the soft tissue in the direction of arrows M, therefore, as the reamer 10 is continually removed from the patient 530, the soft tissue 540 is continually moved in the direction of arrow M, such that the tissue reaches an area, shown in phantom 540', when the reamer 10', shown in phantom, has fully engaged the soft tissue 540', therefore the reamer 10 can be easily removed from the patient 530 without further traumatizing the patient 530.

Therefore, the reamer 10, and various embodiments can be used in a minimally invasive and minimally traumatizing procedure to ream an acetabulum 532. Once the acetabulum 532 is reamed, as described above, an appropriate acetabular implant may be implanted into the reamed acetabulum. In this way, the acetabulum 532 can be prepared for receiving an acetabular implant while only minimally traumatizing the patient 530.

Specifically, the protective wings, as described above and according to various embodiments, can be used to push or move aside the soft tissue during egression of the various acetabular reamers. In addition, the stabilizing or protection bars or sections, further defining portions of the reamer hemisphere, assist in further protecting the soft tissue surrounding the incision both during ingression and egression of the acetabular reamer. Therefore, the soft tissue surrounding the incision 542 will be only minimally traumatized to ream the acetabulum.

In addition, the various stabilizing portions or bars assist in assuring that only a selected orientation of the acetabular reamer is provided. Specifically, the stabilizing portions or bars further define the hemisphere of the acetabular reamer, such that the acetabular reamer cannot easily wobble. Specifically, the acetabular reamer, including the stabilizing portions or members, rotate around a substantially single axis of rotation. In addition, the axis of rotation can be kept at a single location relative to the patient 530. That is, a point after the axis can be selected relative to the patient and the acetabulum 532 and the acetabular reamer kept in that single orientation or along that single point during the entire reaming procedure. This allows for a substantially congruent and symmetrical reamed acetabulum 532 that is substantially complementarily shaped to the acetabular reamer.

Although the above description includes exemplary descriptions of various embodiments, it will be understood that other exemplary embodiments may be provided. For example, the cylindrical portion of the third alternative embodiment of the reamer 300 may be provided with any of the other embodiments to provide for a larger protected or defined area. In addition, the various embodiments of the protective wings can be differently defined to provide for different cross-sections and sizes depending upon a patient and situation of an acetabulum 532 to be reamed.

The description is merely exemplary in nature and, thus, variations that do not depart from the gist are intended to be within the scope of the following claims. Such variations are not to be regarded as a departure from the spirit and scope of the claims.

What is claimed is:

1. A reamer for use in a procedure to ream a selected anatomical portion, the reamer comprising:
   a cutting section having a first edge and a second edge and including all of a cutting portion between the first edge and the second edge and defining a portion of a sphere that has a center wherein the portion of the sphere extends on a first side of a plane defined by an edge of the cutting section, and an axis of rotation;
   a substantially separate stabilizing member having a third edge and a fourth edge extending from said cutting section wherein each of the third edge and the fourth edge are substantially orthogonal to said axis of rotation;
   a protective member extending a distance from a second side of said plane away from the cutting section and adapted to minimize trauma during at least one of ingress and egress of the reamer during the procedure;
   wherein said protective member is adapted to maintain tissue that is surrounding the selected anatomical portion at a selected distance during at least one of ingress and egress of the reamer.

2. The reamer of claim 1, further comprising:
   a plurality of the cutting portions extending from said cutting section.

3. The reamer of claim 2, wherein each cutting portion includes a cutting edge and an opening wherein material that is cut with said cutting edge is able to be transported through said cutting section.

4. The reamer of claim 1, wherein said cutting section defines a portion of about 1° to about 160° of said sphere.

5. The reamer of claim 1, wherein said cutting section defines a first portion of said sphere and said stabilizing member defines a second portion of said sphere.

6. The reamer of claim 1, wherein said protective member includes a substantially smooth surface extending inwardly of a rim that is substantially adjacent said plane.

7. The reamer of claim 1, wherein:
   said cutting section defines a portion of a hemisphere extending towards said plane;
   said protective member extends from away from said plane.

8. The reamer of claim 1, wherein said protective member extends beyond said plane and towards said axis of rotation.

9. The reamer of claim 1, wherein:
   said cutting section defines a first portion of a hemisphere;
   said protective member defines a second portion of said hemisphere;
   said hemisphere being substantially hollow such that material cut by said cutting portion is selectively transported into said hollow hemisphere.

10. The reamer of claim 9, wherein:
    said cutting section defines a first portion of the reamer and said protective member defines a second portion of the reamer wherein voids are defined between said cutting section and said protective member such that a surface may be viewed through said voids.

11. The reamer of claim 9, wherein said cutting section and said protective member are spaced apart from one another over a portion of a perimeter of the cutting section and the protective member.

12. The reamer of claim 1, wherein:
    said cutting section is substantially continuous with said protective member such that the selected anatomical portion is substantially blocked from view of a user of the reamer while the reamer is reaming the selected anatomical portion.

13. An acetabular reamer for entering through a soft tissue and reaming an acetabulum of an individual, comprising:
    a cutting section comprising all of a cutting edge and defining a first portion of a sphere extending from a first plane, wherein the first portion of the sphere defines a surface;
    a stabilizing bar having a first edge and a second edge distinct from the cutting section and extending from said cutting section and defining a second portion of said sphere and the surface; and
    a protective member extending from said stabilizing member;
    wherein said protective member protects the soft tissue during removal of the acetabular reamer from the acetabulum wherein between said cutting section and at least one of said first edge, said second edge, or combinations thereof said stabilizing bar defines a viewing area in the acetabular reamer; wherein said viewing area allows viewing of the acetabulum while the cutting section is positioned substantially adjacent to the acetabulum.

14. The acetabular reamer of claim 13, further comprising:
    a cutting portion including the cutting edge; and
    a cutting opening defined by said cutting section;
    wherein said cutting edge is able to cut a portion of said acetabulum and said cutting opening allows the cut portion of the acetabulum to pass through said cutting section.

15. The acetabular reamer of claim 13, wherein said first portion of a sphere is about 1° to about 160° of said sphere.

16. The acetabular reamer of claim 15, wherein said stabilizing bar defines a further portion of the sphere such that said cutting section and said stabilizing member substantially define a hemisphere.

17. The acetabular reamer of claim 13, further comprising:
    an axis of rotation defined by said cutting section; and
    a tool engaging member extending substantially perpendicular to said axis of rotation such that a tool may engage said tool engaging portion and rotate said cutting section around said axis of rotation.

18. The acetabular reamer of claim 13, wherein said cutting section and said stabilizing member define a substantially continuous hemisphere.

19. The acetabular reamer of claim 13, further comprising:
    an axis of rotation defined by said cutting section about which said cutting section rotates while the acetabulum is reamed;
    wherein said protective member extends towards said axis of rotation.

20. The acetabular reamer of claim 19, wherein said protective member extends from said plane opposite from said cutting section and towards said axis of rotation.

21. The acetabular reamer of claim 13, wherein said stabilizing bar and said protective member cooperate to form a tissue track to position the soft tissue during ingress and egress of the acetabular reamer.

22. The acetabular reamer of claim 13, further comprising:
    a rim operably interconnecting said cutting section and said stabilizing member substantially adjacent said first plane.

23. The acetabular reamer of claim 22, wherein said cutting section, said stabilizing member, and said rim substantially define a void such that the acetabulum may be viewed through said void while the cutting section is substantially positioned in the acetabulum.

24. A reamer for reaming an anatomical portion, comprising:
  a member defining a portion of a sphere having a first interior side and a second exterior side and extending from a plane in a first direction;
  a substantially continuous rim extending from said member defining a perimeter and having a third interior side and a fourth exterior side; and
  the member having a first edge extending from the first interior side to the second exterior side and the rim having an edge extending from the third interior side to the fourth exterior side, wherein a viewing area is defined by the first edge and the second edge wherein both the first edge and the second edge are not cutting edges;
  wherein the anatomical portion is viewable through said viewing area wherein said member includes: a cutting section defining a first portion of said sphere; and a stabilization section defining a second portion of said sphere.

25. The reamer of claim 24, wherein said rim includes:
  a wall;
  wherein said viewing area is defined within said wall.

26. The reamer of claim 24, further comprising:
  an axis of rotation defined by said member; and
  a protective member that extends toward said axis of rotation.

27. The reamer of claim 24, wherein said member includes:
  a cutting section having a cutting portion;
  wherein said cutting section defines less than 180° of said sphere.

28. The reamer of claim 24, wherein the member defines a cutting portion.

29. The reamer of claim 28, wherein the cutting portion includes at least one of a cutting edge, an opening, or combinations thereof.

30. The reamer of claim 29, wherein the viewing area is substantially larger than the opening.

31. A reamer for use in a procedure to ream a selected anatomical portion, the reamer comprising:
  a cutting section having an edge defining a first plane and including substantially all of a cutting edge;
  a protective member having an exterior surface that extends from a second side of said first plane and away from the cutting section wherein the exterior surface defines a curve, is smooth, and adapted to minimize trauma during at least one of ingress and egress of the reamer during the procedure;
  wherein the protective member includes an outer surface that defines a radius over at least a portion of the outer surface;
  wherein said protective member is adapted to maintain tissue, that is surrounding the selected anatomical portion, at a selected distance during at least one of ingress and egress of the reamer wherein the protective member includes an outer edge defining a radius and a first edge that defines a second plane distinct from the first plane.

32. A reamer for use in a procedure to ream a selected anatomical portion, the reamer comprising:
  a cutting section defining a portion of a sphere on a first side of a plane and an axis of rotation around which the cutting section is operable to move in a direction of rotation;
  at least two separate protective members each defining a first edge and a second edge wherein the first edge leads relative to a direction of rotation and the second edge trails relative to the direction of rotation and each extending a distance from a second side of said plane away from the cutting section and adapted to minimize trauma during at least one of ingress and egress of the reamer during the procedure;
  wherein the protective members are segmented near the plane;
  wherein the protective members are adapted to maintain tissue that is surrounding the selected anatomical portion at a selected distance during at least one of ingress and egress of the reamer.

33. The reamer of claim 32 wherein the protective members includes more than two separate protective members.

34. The reamer of claim 33, further comprising:
  stabilizing members defining a portion of the sphere on the first side of the plane and substantially next to but separate from the cutting section and being devoid of a cutting portion;
  wherein at least one of the protective members extends only from the stabilizing member form the second slide of the plane.

* * * * *